United States Patent [19]
Magers

[11] Patent Number: 5,190,863
[45] Date of Patent: Mar. 2, 1993

[54] COMPOSITION FOR DETERMINING THE PRESENCE OR CONCENTRATION OF D-β-HYDROXYBUTYRATE

[75] Inventor: Thomas A. Magers, South Bend, Ind.

[73] Assignee: Miles Inc., Elkhart, Ind.

[21] Appl. No.: 545,634

[22] Filed: Jun. 29, 1990

[51] Int. Cl.$^5$ ............................................. C12Q 1/32
[52] U.S. Cl. ...................................... 435/25; 435/26; 436/128; 436/904; 564/154; 544/85
[58] Field of Search ..................... 435/26, 25; 436/128, 436/904; 564/154; 548/365

[56] References Cited

U.S. PATENT DOCUMENTS

| | | | |
|---|---|---|---|
| 4,147,514 | 4/1979 | Magers et al. | 422/56 |
| 4,279,993 | 7/1981 | Magers et al. | 435/25 |
| 4,288,541 | 9/1981 | Magers et al. | 435/28 |
| 4,290,773 | 9/1981 | Magers et al. | 435/14 |
| 4,318,984 | 3/1982 | Magers et al. | 435/14 |
| 5,041,658 | 8/1991 | Albarella | 564/154 |

*Primary Examiner*—Johnnie R. Brown
*Assistant Examiner*—Pamela S. Webber
*Attorney, Agent, or Firm*—Roger N. Coe

[57] ABSTRACT

A composition, test device and method of determining the presence or concentration of ketone bodies, and specifically D-β-hydroxybutyrate, in a test sample are disclosed. The test device includes a test pad comprising a suitable carrier matrix incorporating an indicator reagent composition capable of interacting with D-β-hydroxybutyrate to produce a detectable or measurable response. In addition, a new and improved indicator reagent composition, comprising a) an indicator dye that is responsive to thiols, such as a substituted isobenzothiazolone, Ellman's reagent or a derivative of Ellman's reagent; b) D-β-hydroxybutyrate dehydrogenase; c) lipoamide dehydrogenase; d) D,L-lipoamide; and e) nicotinamide adenine dinucleotide, is incorporated into the carrier matrix to provide an accurate and sensitive assay of a test sample for D-β-hydroxybutyrate (DHBA) in particular, and for ketone bodies in general. The improved method and composition are especially useful in the assay of whole blood, blood serum, blood plasma and urine for ketone bodies.

23 Claims, 14 Drawing Sheets

COMPOSITION FOR DETERMINING THE PRESENCE OR CONCENTRATION OF D-β-HYDROXYBUTYRATE

FIELD OF THE INVENTION

The present invention relates to a composition and method of determining the presence or concentration of D-β-hydroxybutyrate (DHBA) in particular, and of ketone bodies in general, in a test sample. More particularly, the present invention relates to a new and improved method of assaying a liquid test sample, such as urine, whole blood, blood plasma or blood serum, for ketone bodies, specifically D-β-hydroxybutyrate, by utilizing a stable and sensitive indicator reagent composition. The enzyme-based indicator reagent composition undergoes a detectable or measurable response upon contact with a test sample containing D-β-hydroxybutyrate. The indicator reagent composition of the present invention provides a more accurate and sensitive assay for D-β-hydroxybutyrate, and therefore ketone bodies, by effectively resisting the interfering affects of common test samples components, like glutathione and ascorbate ion, on the indicator dye. Accordingly, the improved sensitivity achieved by the stable indicator reagent composition of the present invention provides an improved method of assaying for ketone bodies, like D-β-hydroxybutyrate, in a test sample, like a biological fluid, such as whole blood, blood serum, blood plasma, or urine.

BACKGROUND OF THE INVENTION

The body usually completely metabolizes fats to carbon dioxide and water. However, if an inadequate amount of carbohydrate is present in the diet, or if a defect in carbohydrate metabolism or absorption is present, the body then metabolizes increasing amounts of fatty acids When large amounts of fatty acids are metabolized, fatty acid utilization is incomplete. Therefore, the intermediate products of fat metabolism appear in the blood and are excreted in the urine. These intermediate products are termed ketone bodies; and include acetoacetic acid, acetone, and β-hydroxybutyric acid. In addition, stress, physical exercise and diabetes can cause an accelerated decomposition of fats and oxidation of fatty acids to increase the concentration of β-hydroxybutyric acid, acetone and acetoacetic acid in the blood and urine. Accordingly, the assay for ketone bodies in a biological fluid can be helpful in the diagnosis, treatment and monitoring of diabetes.

The concentration of ketone bodies present in the urine and blood of a healthy individual is very low to negligible. Whenever increased amounts of fats are metabolized, such as when the carbohydrate intake is restricted or when the diet is rich in fat, the concentration of ketone bodies can increase. If an excess amount of ketone bodies is present in the blood, the condition is termed ketosis; and if an excess of ketone bodies if present in the urine, the condition is termed ketonuria. Ketonuria also is observed from the restricted carbohydrate intake that occurs with fevers, anorexia, gastrointestinal disturbances, fasting, starvation, cyclic vomiting, pernicious vomiting of pregnancy, cachexia, postanesthesia, and as a result of certain neurologic disorders. In general, all three ketone bodies are present in the urine of individuals with ketonuria in the relative proportions of 20% acetoacetic acid, 2% acetone, and 78% β-hydroxybutyric acid. Acetone and β-hydroxybutyric acid are derived from acetoacetic acid.

Diabetes mellitus is the most important disorder associated with ketosis or ketonuria. Diabetes mellitus is a disorder of glucose metabolism, and, in insulin-deficient diabetes, usually the juvenile-onset type, glucose metabolism is sufficiently impaired such that fatty acids are utilized to meet the energy requirements of the body. If diabetes mellitus is untreated, or is inadequately treated, excessive amounts of fatty acids are metabolized. Consequently, ketone bodies accumulate in the blood, i.e., ketosis, and are excreted in urine, i.e. ketonuria. In addition, ketone bodies are excreted from the body in combination with normal basic ions, thereby reducing in the carbon dioxide combining power of the body and causing systemic acidosis, i.e. increased acidity of the blood. Progressive diabetic ketosis causing diabetic acidosis can lead to coma, and eventually death. The term ketoacidosis is frequently used to designate the combined ketosis and acidosis conditions associated with diabetes.

Thus, detection of ketosis or ketonuria in an individual with diabetes mellitus is important and often indicates that a change in insulin dosage or other management procedures is necessary. Therefore, during periods of acute infections, surgery, gastrointestinal disturbances, or stress, and whenever the management routine does not adequately control the disease, the blood or urine of a diabetic individual should be checked for the presence of ketone bodies.

Usually, the presence of ketone bodies has been detected by assaying urine. In ketonuria, the acetoacetic acid, acetone and β-hydroxybutyric acid are excreted in the urine. Consequently, an assay procedure that detects or measures the presence of one of the three ketone bodies usually is satisfactory for the diagnosis of ketonuria. Although specific tests exist for the determination of each of the ketone bodies, the specific tests usually are not used because the methods are more cumbersome, less reliable and less sensitive than the general assay for ketone bodies.

For example, the nitroprusside ion, $(Fe(NO)(CB)_5)^{-2}$, interacts both with acetone and acetoacetic acid in the presence of alkali to produce a purple-colored compound. Thus, sodium nitroprusside assays are specific to acetoacetic acid and acetone and do not detect β-hydroxybutyric acid. This nitroprusside interaction forms the basis of a number of different prior art assays, such as Rothera's test and Legal's test. The present day reagent strip method is the simplest technique for determination of ketonuria The reagent strip is impregnated with sodium nitroprusside and alkaline buffers. The strip is dipped into fresh urine, then compared to the color chart after exactly 15 seconds. The chart has six color blocks indicating negative, trace (5 mg/dL), small (15 mg/dL), moderate (40 mg/dL), large (80 mg/dL), or (160 mg/dL) concentrations of ketones, and ranging in color from buff to lavender to maroon. However, the nitroprusside assay method does not measure the concentration of β-hydroxybutyrate, the major ketone body. Accordingly, the assay result can be a misleading determination of the total amount of ketone bodies in the urine.

For example, studies have shown that assaying urine for acetoacetate by the nitroprusside method failed to detect ketonuria in from about 50% to about of diabetic individuals actually having ketonuria. Coupling this fact of misdiagnosis with the fact that assaying urine for ketones already is a delay in detecting blood ketosis, makes it obvious that a urine assay for acetoacetate is not sufficient to monitor the onset of ketosis in a diabetic individual. Accordingly, the present invention is directed to assaying a biological fluid, such as blood or urine, for the major ketone body, D-β-hydroxybutyric acid, to achieve a sensitive and reliable assay for the onset of ketosis.

Although methods of determining the presence and amount of ketone bodies in urine are available, with advances in blood glucose self-monitoring by diabetic individuals, instances of undetected ketosis have increased. It has been found that as diabetic individuals increasingly use blood glucose monitoring to replace urine glucose testing, urine testing for ketone bodies then is neglected totally and ketonuria goes undetected.

D-β-hydroxybutyric acid is present in the blood at about two to three time the level of acetoacetic acid. The presence of D-β-hydroxybutyric acid in the blood also signifies the onset of ketosis much earlier than the detection of acetoacetare in the urine, and is a much more accurate analyte for monitoring the presence of ketone bodies, and hence, the effectiveness of a particular insulin therapy. For example, often, a sufficient amount of insulin is administered to drive down the glucose level of an individual, but not enough insulin is administered to drive down the level of ketone bodies. Furthermore, under some pathological conditions of the liver, all ketone bodies are converted to D-β-hydroxybutyric acid. Therefore, an assay for acetoacetate could not detect such pathological conditions.

Accordingly, investigators sought methods of accurately detecting D-β-hydroxybutyric acid in the blood. The most widely-used colorimetric test for D-β-hydroxybutyric acid has been the reduction of the colorless dye 2-(4-indophenyl)-3-(4-nitrophenyl)-5-phenyl-tetrazolium chloride hydrate to a colored formazan compound. However, this common dye is highly photosensitive, and is ascorbate and glutathione sensitive.

More particularly, the prior art, such as Japanese Patent Application Number 58-39813, filing date Mar. 8, 1983, disclosed assays for D-β-hydroxybutyric acid (DHBA) wherein the DHBA is oxidized to acetoacetic acid by β-hydroxybutyric acid dehydrogenase in the presence of nicotinamide adenine dinucleatide (NAD). This reaction produces reduced NAD (NAD-H), that in turn interacts with a tetrazolium dye to produce a colored formazan compound. The degree and intensity of the color transition then are correlated to the amount of DHBA in the test sample. In general, the reaction sequence is depicted as:

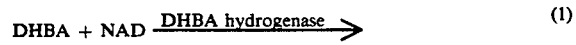

(1)

acetoacetic acid + NAD—H

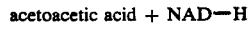

(2)

Similarly, Harano et al., in the publication "Development of Paper-Strip Test for 3-Hydroxybutyrate and Its Clinical Application", *Diabetes Care*, 7, p. 481–485 (1984), disclosed a test strip assay method for DHBA, wherein the reaction sequence is similar to the sequence illustrated above in Equations (1) and (2). In addition, Harano et al., in the publication "Direct Automated Assay Method for Serum or Urine Levels of Ketone Bodies", *Clinica Chimica Acta*, 157, p. 177–183 (1985), disclosed an automated assay based upon the above reaction sequence.

European Patent Application No. 84306671.3 disclosed an assay for DHBA wherein the increasing amount of reduced NAD (NAD-H) generated in Equation (1) of the above sequence was determined photometrically. The assay included the addition of lactic dehydrogenase inhibitor, but did not include an indicator dye. Furthermore, the assay method was a wet assay method as opposed to a dry test strip assay method.

Owen, in U.S. Pat. Nos. 4,254,222 and 4,351,899, disclosed a method of assaying for DBHA based upon the above reaction sequence of Equations (1) and (2), but further included an intermediate electron carrier to more effectively reduce the tetrazolium dye to a formazan compound. Owen disclosed that improved color transitions were observed if the NAD-H reduced an electron carrier, like phenazine methosulfate, and then the reduced phenazine methosulfate reduced the tetrazolium dye to a formazan compound. As will be demonstrated more fully hereinafter, the composition and method of the present invention do not rely upon the tetrazolium reaction illustrated above in Equation 2. The present invention relies upon sequential enzyme-based reactions, and avoids the drawbacks and disadvantages associated with tetrazolium dyes, such as photosensitivity and sensitivity to ascorbate ion and glutathione often present in test samples In contrast to the prior art, the method of the present invention utilizes a reductive pathway based upon lipoamide dehydrogenase (LADH) and a thiol-sensitive indicator dye, such as Ellman's reagent, a derivative of Ellman's reagent or, preferably, a substituted isobenzothiazolone. It has been found that, after the DHBA has reacted with DHBA dehydrogenase and NAD to form NAD-H, LADH then interacts with the NAD-H and D,L-lipoamide to form a thiol compound, 6,8-dimercaptooctamide. The 6,8-dimercaptooctamide then interacts with a thiol-responsive indicator dye, such as Ellman's reagent, a derivative of Ellman's reagent or a suitable isobenzothiazolone. Upon interaction with the thiol compound, the thiol-responsive indicator dye undergoes a detectable or measurable color transition that can be correlated to the amount of DHBA in a test sample.

As stated previously, the presence of ketone bodies in the blood or urine of an individual often is undetected because diabetics presently self-monitor glucose levels in their blood. The assay for ketone bodies is a standard urine assay, but since individuals started self-blood testing, the individuals avoid the bother and/or expense of buying and using a different assay product for use on a separate body fluid to test for another analyte. In addition, diabetics often believe, erroneously, that whole blood self-monitoring of glucose levels relieves the individual from the need to monitor ketones levels. However, if ketone monitoring is ignored, ketosis can go undetected, and the patient can slip into diabetic ketoacidosis, a common illness among patients with diabetes and having a mortality rate as high as 10%.

Therefore, uncontrolled diabetes has two important consequences. The first consequence is an alteration in glucose production and disposal, and the second is accelerated ketogenesis, i.e. ketone formation. These two consequences are closely connected because the metabolism of carbohydrates and lipids in the liver are tightly coupled, with elevated concentrations of acetoacetate and DHBA in the plasma of individuals with diabetic ketoacidosis due to accelerated synthesis of ketones in the liver and to the finite capacity of peripheral tissues to use these ketones.

Activation of ketogenesis requires the mobilization of long-chain fatty acids from stores in adipose tissue and a change in hepatic metabolism such that incomplete fatty acids are oxidized to ketone bodies rather than re-esterified to form triglycerides for transport out of the liver as very low-density lipoproteins. The mobilization of fatty acids is induced by insulin deficiency, whereas the oxidation of fatty acids is induced by a rise in glucagon/insulin ratio.

Ketone bodies then are metabolized by the body, with the ratio of DHBA to acetoacetate being extremely variable. However, the DHBA is the predominant component. The increasing levels of DHBA, as reflected in an increasing DHBA/acetoacetate ratio, correlates to the concentration of available free fatty acid. Since the rate of oxidation of the fatty acids is directly related to their plasma level, fatty acid concentration can determine the equilibrium between acetoacetate and β-hydroxybutyrate. Therefore, a decreasing fatty acid oxidation can alter this equilibrium in favor of acetoacetate and result in a lower DHBA/acetoacetate ratio. Conversely, a very high DHBA/acetoacetate ratio is observed when fatty acid levels rise.

Insulin also has an immediate impact on the DHBA/acetoacetate ratio. A rapid decrease of the ratio occurs after administration of insulin. This effect is unrelated to the dose of insulin and is observed both in individuals with ketoacidosis and individuals attempting to stabilize of diabetes. The decrease of the DHBA/acetoacetate ratio is attributed to a delayed decrease in acetoacetate concentration, a concentration that can remain unchanged for hours and that can persist for days after commencement of ketoacidosis treatment. In fact, acetoacetate levels actually can increase during this period. Therefore, because the concentration of acetoacetate can increase, and at least remains unchanged, for several hours during ketoacidosis treatment, an assay for acetoacetate cannot reliably monitor the progress of the treatment.

Accordingly, the sensitive rise and fall of DHBA concentration at the onset of, and during treatment of, ketoacidosis signifies that DHBA should be the primary analyte for detecting and monitoring ketosis. For example, in terms of millimolar quantities, the extent of the rise and fall of blood levels of DHBA is greater than acetoacetate or glucose. Accordingly, an assay for DHBA provides the most sensitive monitor of ketosis and ketoacidosis among the various analytes that are symptomatic of ketosis.

Present-day technology has changed glucose self-monitoring from the rather inexact and post facto urine testing to the more sensitive metabolic control of blood glucose. Blood glucose monitoring is replacing urine testing since blood self-monitoring permits control of glycemia in the near-normal range. As a result, urinary ketone self-monitoring has been neglected. Apparently, the success of whole blood glucose self-monitoring has led individuals to neglect the monitoring of ketone levels in the blood or urine to signal the onset of ketosis. Therefore, because individuals and doctors have neglected testing for urine ketones, the development of a dry phase reagent test strip suitable to detect and measure blood ketone concentration would be useful for individuals monitoring an illness at home.

It has been demonstrated that any wet phase or dry phase assay that monitors only acetoacetate is unreliable as a monitor of the onset of ketosis. Therefore, due to the intimate interrelationship between glucose metabolism and ketone body metabolism in an individual with diabetes mellitus, it is apparent that the diabetic population that does whole blood glucose self-monitoring also needs a whole blood test for β-hydroxybutyrate. As previously noted, the availability of test strips for blood glucose self-monitoring has increased the possibility of ketosis going undetected because individuals neglect urine testing, and the individual then fails to detect the onset of ketonuria. Thus, the availability of a dry phase reagent test strip for ketone bodies in blood would help prevent diabetic ketoacidosis. Further, if an individual because of preference or economics desires to monitor the onset of ketosis by urine testing for ketonuria, a sensitive and reliable urine assay to detect ketonuria should detect and measure DHBA. DHBA always is present in the urine in a greater concentration than acetoacetate, and therefore is the most sensitive and reliable analyte for the detection of ketonuria, and therefore, ketosis Therefore, for an individual to detect the onset of ketosis or ketonuria, accurate and sensitive assays of whole blood, blood serum, blood plasma, urine and other test samples for ketone bodies are needed for both laboratory and home use. The assays should permit the detection and measurement of the ketone bodies in the test sample such that a correct diagnosis can be made and correct medical treatment implemented, monitored and maintained. In addition, it would be advantageous if the assay method utilizes a dry phase test strip, in either a wipe-off, a blot-off or a dip-and-read format, for the easy and economical, qualitative or quantitative determination of ketone bodies in blood, urine or other test samples.

Furthermore, any method of assaying for ketone bodies in blood, urine or other test sample should yield accurate, trustworthy and reproducible results by utilizing an indicator reagent composition that undergoes a color transition as a result of an interaction with a ketone body, like DHBA, and not as a result of a competing chemical or physical interaction, such as a preferential interaction with a test sample component other than a ketone body or a color transition occurring due to the instability of the indicator reagent composition. Moreover, it would be advantageous if the assay method for ketone bodies is suitable for use in dry phase reagent test strips for the rapid, economical and accurate determination of a ketone body in blood, urine or other test sample. Additionally, the method and composition utilized in the assay for ketone bodies should not adversely affect or interfere with the other test reagent pads that are present on a multideterminant reagent test strip.

Therefore, in order to determine if an individual is excreting ketone bodies or has an elevated amount of ketone bodies in the blood, and in order to monitor the course of medical treatment to determine the effectiveness of the treatment, simple, accurate and inexpensive detection assays for ketone bodies have been developed. Furthermore, of the several different assay methods developed for the detection or measurement of ketone bodies in urine, the methods based on dip-and-read dry phase test strips have proven especially useful because dry phase test strip methods are readily automated and provide reproducible and accurate results.

Some test strips used in assays for ketone bodies have a single test area consisting of a small square pad of a suitable carrier matrix impregnated with an indicator reagent composition comprising an indicator dye, such as a tetrazolium dye; NAD; and DHBA dehydrogenase. Other test strips are multideterminant reagent strips that include one test area for the assay of ketone bodies as described above, and further include several additional test areas on the same strip to permit the simultaneous assay of other test sample constituents. For both types of colorimetric test strips, the assay for ketone bodies is performed simply by contacting the colorimetric test strip with a blood or urine or other test sample, then comparing the resulting color of the test area of the test strip to a standardized color chart provided on the colorimetric test strip bottle, or determining the color change using a photometer. Ketone body tests usually are included on multideterminant reagent strips to screen urine samples during routine physical examinations. However, ketone body tests usually are not included on reagent strips used to assay blood samples.

The test strip method is the simplest and most accurate direct assay for the presence of ketone bodies in a biological fluid. In prior art test devices, the test area is impregnated with a tetrazolium indicator dye, NAD, and DHBA dehydrogenase. The test area transforms color when ketone bodies present in the test sample react with the DHBA dehydrogenase, NAD and tetrazolium dye in the test pad. In accordance with the above-described prior art method, an individual then can determine the concentration of a ketone bodies in a test sample from the color transition of the tetrazolium dye.

As will be discussed more fully hereinafter, investigators have found that tetrazolium dyes often are photosensitive and are subject to interfering interactions with common test sample components, such as glutathione and ascorbate, that substantially reduce the sensitivity and accuracy of the assay. Therefore, it would be extremely advantageous to have a simple, accurate and trustworthy method of assaying blood, urine and other biological fluids for ketone bodies. Present-day test strips for ketone bodies generally are not available for assaying blood and have the disadvantages of indicator dye instability and interference from test sample components. Surprisingly and unexpectedly, the composition and method of the present invention provide a stable indicator reagent composition that can be used in the assay of blood, urine or other biological fluids for ketone bodies. By providing a more accurate method of determining the concentration of ketone bodies in a test sample, in an easy to use format, such as a dip-and-read, a wipe-off or a blot-off test strip, the assay can be performed by laboratory personnel to afford immediate and trustworthy test results. In addition, the test strip method can be performed by the individual at home to more precisely monitor the level of ketone bodies in blood or urine and/or the success of the medical treatment the individual is undergoing.

The method of the present invention allows the fast, accurate and trustworthy assay for ketone bodies by utilizing a test strip that includes a test pad comprising a suitable carrier matrix impregnated with an indicator reagent composition of the present invention. The indicator reagent composition comprises a thiol-responsive indicator dye, such as Ellman's reagent, a derivative of Ellman's reagent or a substituted isobenzothiazolone; D-$\beta$-hydroxybutyrate dehydrogenase (DHBA dehydrogenase); lipoamide dehydrogenase (LADH); D,L-lipoamide; and nicotinamide adenine dinucleotide (NAD). The indicator reagent composition is sensitive to low concentrations of the ketone body D-$\beta$-hydroxybutyric acid (DHBA); is specific to DHBA; and essentially eliminates the problem of indicator dye and indicator reagent composition instability that leads to inaccurate and insensitive assays. Accordingly, the improved stability and selectivity of the indicator reagent composition enhance the sensitivity of the assay for DHBA, thereby providing a more accurate and trustworthy assay for ketone bodies.

Prior to the present invention, no known method of assaying blood, urine or other test samples for ketone bodies included an indicator reagent composition comprising a thiol-responsive indicator dye; DHBA dehydrogenase; LADH; D,L-lipoamide; and NAD to provide a stable and selective indicator reagent composition. Consequently, the improved stability and selectivity of the indicator reagent composition increase the sensitivity of the assay such that accurate and trustworthy assays for ketone bodies are achieved. Although a dry phase test strip including a tetrazolium indicator dye; NAD; and DHBA dehydrogenase has been used previously, dry phase test strips incorporating these compounds demonstrated an instability to light and a tendency to interact with various common test components. Accordingly, this instability and nonselectivity decreased the accuracy and the sensitivity of the test strip to the ketone bodies in the test sample.

In general, dry phase test strips are more advantageous than the wet phase assays because the test strip format is easier to use, requiring neither the continual preparation of reagents nor the attendant apparatus. In addition, reagent stability is greater in the test strip, thereby resulting in improved assay accuracy, sensitivity and economy. Notwithstanding that dry phase test strips for determining ketone bodies are more stable and more sensitive than wet phase assays, present day test strips for ketone bodies still need improvement in the areas of stability, selectivity and sensitivity. Therefore, it would be a significant advance in the art of diagnostic assays if test strips were even more stable during storage and even more selective and sensitive to ketone bodies. It was towards achieving these improvements that the investigations resulting in the composition, device and method of the present invention were directed.

Some attempts at achieving the above-mentioned goals of increased stability and sensitivity are found in the previously-discussed prior art. In contrast to the prior art, and in contrast to the presently available commercial test strips, the composition of the present invention imparts increased stability and improved selectivity to the test strip, and therefore increased sensitivity of the test strip, in the detection and measurement of ketone bodies in a test sample. The method of the present invention utilizes a stable indicator reagent composition that effectively resists degradation of the indicator dye and interacts specifically with the ketone body DHBA present in the test sample. Surprisingly and unexpectedly, the method and composition of the present invention essentially eliminate color formation, or other detectable responses, attributable to indicator dye interaction with test sample components other than DHBA. Hence, in accordance with the method of the present invention, new and unexpected results are achieved in the dry phase test strip assay of blood, urine and other test samples for ketone bodies by utilizing stable, selective and sensitive indicator reagent composition.

SUMMARY OF THE INVENTION

In brief, the present invention is directed to a new and improved composition, test device and method of determining the presence or concentration of a predetermined component in a test sample. The device includes a test pad comprising a suitable carrier matrix incorporating an indicator reagent composition capable of interacting with a predetermined test sample component to produce a detectable response. For home use, the indicator reagent composition produces a visually detectable response. For laboratory use, the indicator reagent composition produces a response that is detectable visually or by instrument. The carrier matrix of the test pad comprises a bibulous material, such as filter paper; a nonbibulous material, such as a strip, layer or membrane of a polymerized material; or combinations thereof. An indicator reagent composition is homogeneously incorporated into the carrier matrix, and the carrier matrix then holds the indicator reagent composition homogeneously throughout the carrier matrix while maintaining carrier matrix penetrability by the predetermined component of the test sample.

More particularly, the present invention is directed to a method of assaying blood, urine or other test samples for ketone bodies by utilizing a new and improved indicator reagent composition. It has been demonstrated that an indicator reagent composition comprising:

(a) a thio-sensitive indicator dye, like Ellman's reagent, a derivative of Ellman's reagent or a substituted isobenzothiazolone having the general structural formula:

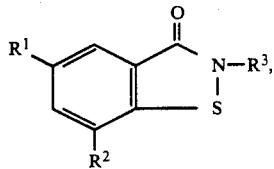

wherein at least one of the $R_1$ and $R_2$ substituents is selected from the group consisting of nitro, arylazo, substituted arylazo, benzylideneamino and substituted benzylideneamino, such that when only one of $R_1$ and $R_2$ is so substituted, one of $R_1$ and $R_2$ can be hydrogen; and the $R_3$ substituent is selected from the group consisting of alkyl, carboxylalkyl, hydroxyalkyl, aminoalkyl, haloalkyl, aryl, carboxyaryl, hydroxyaryl, aminoaryl, heteroaryl, carboxyheteroaryl, hydroxyheteroaryl, aminoheteroaryl, hydroxy, alkoxy, amino and substituted derivatives thereof;

(b) D-$\beta$-hydroxybutyric acid dehydrogenase (DHBA dehydrogenase);

(c) lipoamide dehydrogenase (LADH);

(d) D,L-lipoamide; and (e) nicotinamide adenine dinucleotide (NAD), demonstrates improved stability and increased selectivity and sensitivity towards the ketone body DHBA in a test sample.

In accordance with an important feature of the present invention, a more accurate and reliable qualitative or quantitative determination of ketone bodies in a test sample is achieved because the indicator reagent composition exhibits improved indicator dye stability prior to contact between the indicator reagent composition and a test sample including ketone bodies, and exhibits improved selectivity because the indicator reagent composition does not interact with common interfering components often found in test samples. By utilizing the indicator reagent composition of the present invention in clinical test methods, the qualitative or quantitative assay for a ketone body, such as D-$\beta$-hydroxybutyric acid (DHBA), in blood, urine or other biological or nonbiological test samples is more sensitive and accurate.

Therefore, it is an object of the present invention to provide a new and improved method and test device for determining the relative concentration of a predetermined chemical compound in a liquid test sample.

Another object of the present invention is to provide a simple, trustworthy, accurate and reproducible method of assaying urine, whole blood, blood plasma, blood serum, and other test samples for ketone bodies.

Another object of the present invention is to provide a method of assaying whole blood, blood plasma, blood serum, urine or other liquid test samples for ketone bodies by utilizing a stable and specific indicator reagent composition that provides increased sensitivity and accuracy in the assay for the ketone body DHBA.

Yet another object of the present invention is to provide a sensitive method of assaying biological test samples for the ketone body DHBA in a concentration range of from 0 mmol/L to about 60 mmol/L (millimoles of DHBA per liter of test sample).

Another object of the present invention is to provide a method of assaying whole blood, blood serum, blood plasma, urine or other liquid test samples for DHBA that is sufficiently sensitive to quantitatively detect DHBA in concentrations as low as about 0.1 mmol/L.

Another object of the present invention is to provide a method of assaying whole blood, blood serum, blood plasma, urine or other biological test liquids for ketone bodies utilizing an indicator reagent composition comprising a thiol-responsive indicator dye; DHBA dehydrogenase; LADH; D,L-lipoamide; and NAD, wherein the indicator reagent composition is stable upon storage and exposure to light, and selectively interacts essentially only with the DHBA present in the biological test liquid.

Another object of the present invention is to provide a method of assaying whole blood, blood serum, blood plasma, urine or other biological test samples by utilizing a stable indicator reagent composition that effectively maintains the activity of the indicator dye prior to contacting the test sample and that, upon contact with the test sample, interacts selectively with a ketone body in the test sample to undergo a detectable and measurable color transition to establish the presence or concentration of the ketone body in the test sample.

Another object of the present invention is to provide a new and improved test device for interaction with the ketone body DHBA in a test sample to produce a visible change, such as a change in color, of the test device, indicative of the concentration of DHBA in the test sample.

Another object of the present invention is to provide a composition and test device that are sensitive to low concentrations of a ketone body, demonstrate excellent resistance to ascorbate and glutathione interferences, have excellent storage stability and essentially eliminate inaccurate assay results for a ketone body.

Still another object of the present invention is to provide a stable indicator reagent composition capable of undergoing a color transition upon contact with DHBA, wherein the indicator reagent composition comprises a thiol-responsive indicator dye, such as Ellman's reagent, a derivative of Ellman's reagent or an isobenzothiazolone having the general structural formula

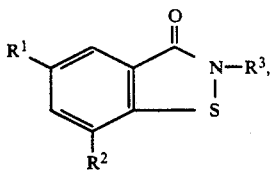

wherein at least one of the R₁ and R₂ substituents is selected from the group consisting of nitro, arylazo, substituted arylazo, benzylideneamino and substituted benzylideneamino, such that when only one of R₁ and R₂ is so substituted, one of R₁ and R₂ can be hydrogen; and the R₃ substituent is selected from the group consisting of alkyl, carboxyalkyl, hydroxyalkyl, aminoalkyl, haloalkyl, aryl, carboxyaryl, hydroxyaryl, aminoaryl, heteroaryl, carboxyheteroaryl, hydroxyheteroaryl, aminoheteroaryl, hydroxy, alkoxy, amino and substituted derivatives thereof; D-β-hydroxybutyric acid dehydrogenase (DHBA dehydrogenase); lipoamide dehydrogenase (LADH); D,L-lipoamide; and nicotinamide adenine dinucleotide (NAD).

BRIEF DESCRIPTION OF THE DRAWINGS

The above and other objects, advantages and novel features of the present invention will become apparent from the following detailed description of the present invention taken in conjunction with the drawing wherein.

DETAILED DESCRIPTION OF THE INVENTION

Figure 1:
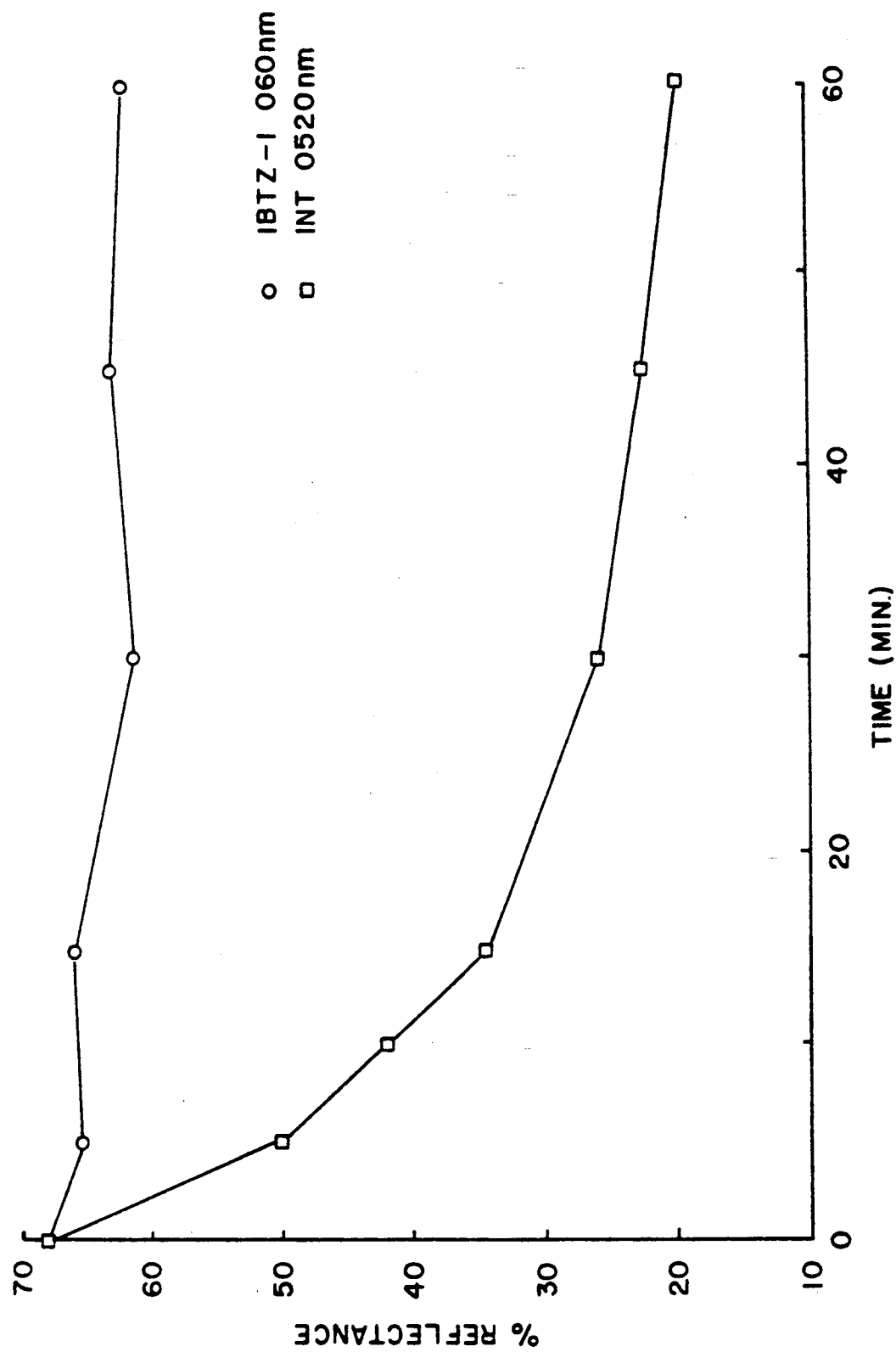
FIG. 1 is a plot of percent reflectance vs. time for dry phase test strips incorporating either the tetrazolium dye INT or the isobenzothiazolone dye IBTZ-I as the indicator dye and exposed to combined daylight and ultraviolet radiation for 60 minutes.

In accordance with the method of the present invention, the qualitative or quantitative assay for a ketone body, D-β-hydroxybutyric acid (DHBA), in whole blood, blood serum, blood plasma, urine and other test samples is accomplished by utilizing a stable and selective indicator reagent composition comprising a thiol-responsive indicator dye; D-β-hydroxybutyrate dehydrogenase (DHBA dehydrogenase); lipoamide dehydrogenase (LADH); D,L-lipoamide; and nicotinamide adenine dinucleotide (NAD). By employing the stable indicator reagent composition of the present invention, the indicator dye maintains its activity prior to contact between the indicator reagent composition and the test sample. The indicator dye, after contacting a test sample including DHBA, readily undergoes a color transition or other detectable transformation in response to an interaction with the reduced form of D,L-lipoamide (i.e., 6,8-dimercaptooctamide) that is generated by the interaction of the DHBA dehydrogenase, NAD and LADH present in the indicator reagent composition with the DHBA present in the test sample.

The prior art assays for DHBA, either wet phase or dry phase, were based upon a tetrazolium compound as the indicator dye in the oxidation-reduction reaction to detect DHBA. The prior art assays generally were based upon the following reaction sequence, wherein a colorless tetrazolium dye was transformed into a colored formazan compound:

   (1)

-continued $$\text{acetoacetic acid} + \text{NAD}-\text{H}$$

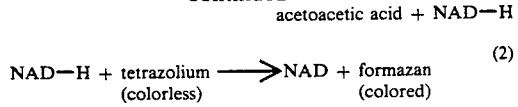

However, this tetrazolium dye is relatively unstable and the assay is subject to interfering compounds often present in biological test samples, like ascorbate ion and glutathione. Accordingly, the composition and method of the present invention eliminate the tetrazolium-based chemistry, and utilize lipoamide dehydrogenase chemistry to transform a thiol-responsive indicator dye from a first color to a second color. Preferably, the first color is colorless and the second color is a deep, or intense, color; or conversely, the first color is a deep color and the second color is colorless. Such color transitions are more differentiable and resolvable, and therefore provide more sensitive and accurate assays. Furthermore, it has been found that the lipoamide dehydrogenase chemistry utilized in the present invention provides a stable indicator reagent composition that is selective for DHBA and is not subject to interference from compounds normally found in biological systems.

In particular, the present invention utilizes a coupled enzyme system, wherein the enzymes DHBA dehydrogenase and LADH interact with their particular substrates, in sequence, to provide a detectable and measurable color change that can be correlated to the amount of DHBA in the test sample. Accordingly, the DHBA dehydrogenase and LADH react in sequence, as shown in the following reaction scheme, in an assay for the presence or concentration of DHBA in a test sample.

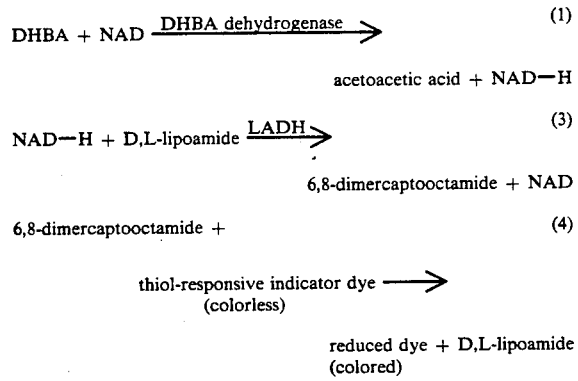

As will be demonstrated more fully hereinafter, the composition and method of the present invention essentially eliminate the disadvantages and problems associated with a tetrazolium-based assay for DHBA. Accordingly, the accuracy and the sensitivity of the DHBA assay are increased. The improved accuracy and increased sensitivity to DHBA afforded by the method of the present invention are especially useful in blood assays for DHBA.

A commercially useful assay for DHBA must be stable, sensitive and resistant to interfering compounds, like ascorbic acid. The stability and sensitivity requirements for a useful DHBA assay have been defined as a sensitivity of at least 0.5 mmol/L DHBA in the test sample. In addition, as previously discussed, ascorbic acid and glutathione are common interferents in assays based on redox indicator dyes. In particular, ascorbic acid interferences in assays for DHBA are well known in the art and should be eliminated. Ascorbate resistance therefore is defined as a negligible interference with the color transition of the indicator dye when a test sample contains as much as approximately 50 mg (milligrams) ascorbic acid per deciliter (dL) of sample.

Present day commercial assays for a ketone body, like DHBA, can detect concentrations as low as about 0.5 mmol/L in urine and about 0.05 mmol/L in blood. The urine or blood of a healthy individual is essentially free of ketone bodies. Therefore, detecting a low concentration of ketone bodies in biological fluids is clinically important because ketone bodies in the fluid can signify a diseased or damaged condition that should be investigated further. Accordingly, and as will be discussed more fully hereinafter, the method and device of the present invention accurately assay for a low concentration of ketone bodies in biological fluids, and therefore provide a reliable signal for the onset of ketosis. The composition used in the method and device of the present invention is stable, resists ascorbate and glutathione interferences, and undergoes a color transition only in response to the concentration of DHBA in the test sample, thereby providing a sensitive and reliable assay for ketone bodies.

Furthermore, it will become apparent that the method and device of the present invention can be used to determine the presence or quantitative concentration of ketone bodies in whole blood, blood plasma, blood serum, and urine and more generally, the ketone body concentration of many other biological fluids as well. In general, any aqueous test sample, or test sample that is soluble in an aqueous solvent, can be assayed. In accordance with another important feature of the present invention, the method and composition of the present invention can be employed in dry phase test strip assays to determine the presence or concentration of ketone bodies in blood, urine or other test samples.

The method and test device utilizing the composition of the present invention provide a more accurate, trustworthy and clinically significant assay for DHBA because the thiol-responsive indicator dye undergoes a color transition only in response to the amount of DHBA in the test sample, and not in response to ascorbic acid or glutathione that often are present in the test sample. Furthermore, a method of fast, accurate, reproducible and trustworthy assays for ketone bodies, performable at home or in the laboratory to yield essentially immediate assay results, is achieved.

The method of the present invention utilizes the ability of LADH, in the presence of reduced NAD (NAD-H), to reduce D,L-lipoamide to 6,8-dimercaptooctamide. In an important feature of the present invention, the enzyme LADH interacts with D,L-lipoamide, in sequence, after the enzyme DHBA dehydrogenase first interacts with DHBA and NAD to produce reduced NAD, i.e. NAD-H. The LADH interacts with the D,L-lipoamide and NAD-H (Eq. 3) to produce 6,8-dimercaptooctamide. The 6,8-dimercaptooctamide includes two thiol moieties that can interact with the thiol-responsive indicator dye to yield a reduced form of the indicator dye. Usually, the reduced form of the indicator dye has a different color from the oxidized form of the indicator dye, and the degree and intensity of the color transition are directly proportional to the concentration of DHBA in the test sample. It should be noted that other detectable changes, such as turbidity, also can be used to detect the presence and concentration of DHBA in a test sample. Accordingly, the indicator reagent composition of the present invention includes a pair of coupled enzymes, NAD, D,L-lipoamide and a thiol-responsive indicator dye, wherein the indicator dye undergoes a color transition upon conversion to its reduced form by a thiol formed by the mediation of enzymes, NAD and D,L-lipoamide on the DHBA present in the test sample.

The indicator reagent composition of the present invention, capable of detecting DHBA, and therefore capable of detecting ketone bodies, includes the enzyme, D-$\beta$-hydroxybutyrate dehydrogenase (DHBA dehydrogenase). This enzyme is capable of converting DHBA to acetoacetate, and generally is included in the indicator reagent composition in an amount ranging from 50 units to about 5000 units, and preferably from about 90 units to about 500 units, wherein a unit is defined as the amount of enzyme needed to convert one micromole of DHBA to acetoacetate per minute at pH 8 and 37° C. Within these ranges, sufficient DHBA dehydrogenase is present in the indicator reagent composition for a relatively fast conversion of DHBA to acetoacetate. DHBA dehydrogenase is a common, commercially-available enzyme, available from numerous sources, such as Sigma Chemical Co., St. Louis, Mo.

In addition to the DHBA dehydrogenase, nicotinamide adenine dinucleotide (NAD) also is included in the composition of the present invention. As illustrated in Eq. 1, the DHBA in the test sample is oxidized enzymatically to acetoacetate by the DHBA dehydrogenase, and the NAD is reduced to NAD-H. The reduced form of NAD then is utilized in the next reaction step, i.e. the reduction of D,L-lipoamide by LADH (Eq. 3). The NAD is included in the composition of the present invention in an amount ranging from about 10 mM (millimolar, or millimoles per liter of indicator reagent composition) to about 500 mM, and preferably from about 40 mM to about 100 mM. In general, the amount of NAD included in the composition is limited only in that a sufficient amount is present to allow complete conversion of DHBA to acetoacetate by DHBA dehydrogenase. NAD also is a common, commercially-available enzyme from sources such as TCI American, Portland, OR. or Sigma Chemical Co., St. Louis, Mo.

Both the prior art and the method of the present invention utilize the conversion of DHBA to acetoacetate by DHBA dehydrogenase and NAD (Eq.1). However, the prior art then utilizes the NAD-H formed in Eq. 1 to interact with a tetrazolium dye, either directly or through an intermediate electron carrier, to form a colored formazan (Eq.2). However, the present invention eliminates the unstable tetrazolium dyes, but utilizes the conversion of D,L-lipoamide to 6,8-dimercaptooctamide by the NAD-H generated in Eq. 1 and the enzyme LADH (Eq. 3).

D,L-lipoamide is a compound having the following structural formula (I).

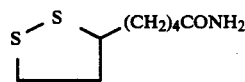
 (I)

D,L-lipoamide, also known as D,L-6,8-thioctamide, is a commercially available compound from a source such as TCI American, Portland, Org. or Sigma Chemical Co., St. Louis, Mo. D,L-Lipoamide is included in the indicator reagent composition of the present invention in a concentration of from about 10 mM (millimolar) to about 200 mM, and preferably in concentration of from about 50 mM to about 150 mM. In general, the amount of D,L-lipoamide included in the composition is limited only in that a sufficient amount is present to allow complete conversion of the reduced NAD (NAD-H) formed in Eq. 1 back to NAD. It also should be understood that substituted derivatives of D,L-lipoamide can be utilized in the composition of the present invention.

The disulfide linkage in D,L-lipoamide, or its substituted derivatives, can be reduced by lipoamide dehydrogenase (LADH), in the presence of reduced NAD (NAD-H) to produce the dithiol 6,8-dimercaptooctamide, illustrated as structural formula (II). This reaction, illustrated generally in Eq. 3 above, and more particularly below in Eq. 3a, is important in the method of the present invention for detecting the presence or concentration of DHBA in a test sample. It can be seen that the NAD-H generated in

 (3a)

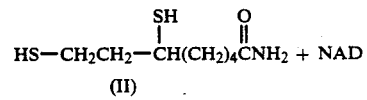
(II)

Eq. 1 can react with D,L-lipoamide (I), in the presence of LADH, to regenerate NAD and to generate the dithiol compound (II). Accordingly, D,L-lipoamide and LADH are essential ingredients in the indicator reagent composition of the present invention. The LADH reduces the disulfide linkage of the D,L-lipoamide (I) to generate the dithiol compound (II) that then can interact with the thiol-responsive indicator dye. Therefore, in addition to the D,L-lipoamide, the indicator reagent composition also includes the enzyme lipoamide dehydrogenase to enzymatically catalyze the reduction of D,L-lipoamide or a derivative of D,L-lipoamide to a dithiol compound.

The LADH enzyme is included in the composition of the present invention in an amount ranging from about 100 units to about 2000 units, and preferably from about 250 units to about 1000 units, wherein a unit is defined as the amount of enzyme that reduces 1 $\mu$mole (micromole) of D,L-lipoamide to D,L-dihydrolipoamide per minute at pH 6.5 and 25° C. LADH also is commercially-available compound from a source such as Sigma Chemical Co., St. Louis, Mo.

It should be noted that in addition to the D,L-lipoamide and LADH disulfide reductase system, other disulfide reductase systems also can be used in the method and composition of the present invention. In each system, an enzyme, i.e. the disulfide reductase, like LADH, reduces a disulfide linkage in the substrate molecule, i.e. the disulfide substrate, like D,L-lipoamide, to provide thiol moieties that then are available to interact with the thiol-responsive indicator dye. TABLE I illustrates nonlimiting examples of disulfide systems that can be used in the present invention. However, it is envisioned that any reductase system that generates a thiol moiety can be utilized in the composition and method of the present invention. As discussed above, the preferred disulfide substrate is D,L-lipoamide, and derivatives thereof, that can be reduced by lipoamide dehydrogenase (LADH).

TABLE I

| Disulfide Reductase Systems | |
|---|---|
| Disulfide Substrate | Disulfide Reductase |
| L-cystine | cystine reductase |
| oxidized glutathione | glutathione reductase |
| lipoamide | lipoamide dehydrogenase |
| protein disulphide | protein disulphide reductase |
| oxidized thioredoxin | thioredoxin reductase |
| CoAS-Sglutathione | CoAS-Sglutathione reductase |
| asparagusate | asparagusate reductase |

In addition to the enzyme LADH, the enzyme DHBA dehydrogenase, the NAD and the D,L-lipoamide, the composition of the present invention includes a thiol-responsive indicator dye. The indicator dye included in the indicator reagent composition is limited only in that the indicator dye is capable of undergoing a detectable response, and preferably a chromogenic response, in the presence of a thiol. Accordingly, the indicator dye preferably is a redox indicator that undergoes a color transition, or other detectable response, upon conversion from its oxidized state to its reduced state by thiol generated in the enzymatic interactions with DHBA and D,L-lipoamide. The indicator dye should be sufficiently stable such that a thiol is present before a color transition occurs. To achieve the full advantage of the present invention, the indicator dye undergoes a color transition through various detectable and measurable degrees and intensities of color such that the degree or intensity of the color transition can be correlated to the concentration of DHBA in a test sample.

A particular thiol-sensitive indicator dye that is useful in the present invention is Ellman's reagent, 5,5'-dithio(2-nitrobenzoic acid), a disulfide compound having the structural formula (III). In the presence of a thiol, Ellman's reagent produces the yellow color of p-nitrophenol at 405 nm (nanometers). Therefore, Ellman's reagent undergoes a color

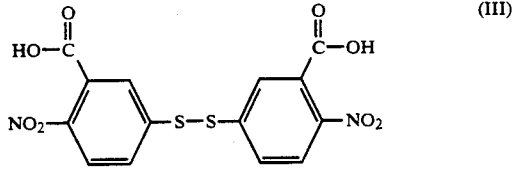
(III)

transition of from colorless to yellow upon interaction with the 6,8-dimercaptooctamide generated in Eq. 3. This interaction is illustrated generally as Eq. 4, and more particularly as Eq. 4a.

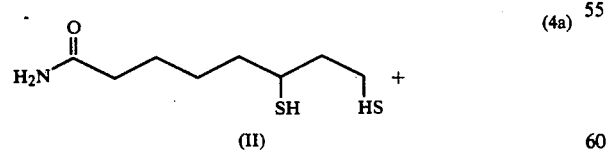
(II)

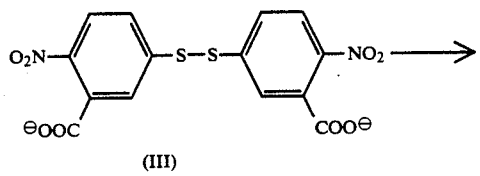
(III)

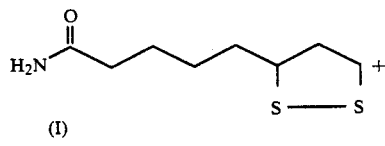
(I)

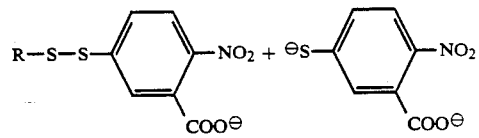

Ellman's reagent is a stable indicator dye and its color transition is sufficiently differentiable to allow correlation of the intensity and degree of the color transition to the concentration of DHBA in the test sample. However, although the color transition of from colorless to yellow can make visual differentiation between color levels difficult, color level differences from colorless to yellow are easily distinguished by color-measuring instruments, such as a colorimeter or a spectrophotometer.

In addition to Ellman's reagent, derivatives of Ellman's reagent also can be used as an indicator dye in the method and composition of the present invention. For example, changing the hydroxyl moiety of the carboxylic acid groups has provided useful derivatives of Ellman's reagent. Therefore, examples of derivatives of Ellman's reagent found useful in the indicator reagent composition of the present invention include, but are not limited to, the various positional isomers of the compound illustrated in structural formula (IV):

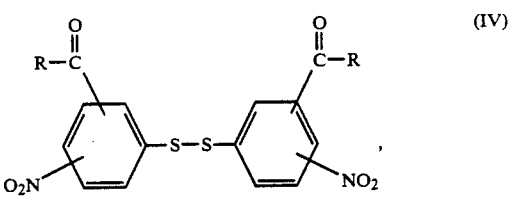
(IV)

wherein R is the residue of an alcohol or an amine to provide an ester or an amide linkage. Examples of alcohol and amine residues found to be useful include, but are not limited to,

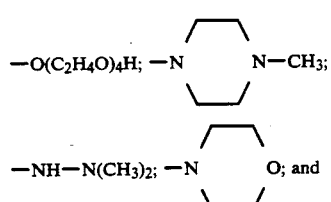

—NH(C₃H₆)N(CH₃)₂.

Water-soluble derivatives of Ellman's reagent are especially preferred; however, water-insoluble derivatives also are useful in the method and composition of the present invention. A particularly preferred water-soluble derivative of Ellman's reagent is 3-N-(3-dimethylaminopropyl)carboxamido-4-nitrophenyl disulfide, illustrated as structural formula (V).

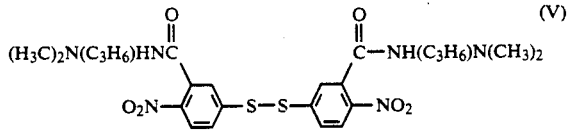

This compound, like Ellman's reagent, is colorless in the oxidized form and exhibits a yellow color in the presence of lipoamide, NADH and lipoamide dehydrogenase. Other commonly-used indicator dyes for the detection of thiols include the 2,2'- and 4,4'-dipyridyl disulfides, like 2,2'-dithiobis(5-nitropyridine) that exhibits an absorption at 340 nm in the reduced form.

The thiol-responsive indicator dye usually is present in the indicator reagent composition in a concentration of from about 10 mM to about 200 mM, and preferably in a concentration of from about 25 mM to about 150 mM. It should be understood that the amount of indicator dye in the indicator reagent composition can be less than about 10 mM, or greater than about 200 mM, depending upon the intensity of the color transition that a particular indicator dye undergoes upon reduction. In general, the amount of indicator dye included in the indicator reagent composition is limited only in that the indicator dye must undergo a detectable color transition for a qualitative assay or, for a quantitative assay, must undergo a measurable color transition in proportion to the amount of DHBA in the test sample.

In addition to Ellman's reagent, derivatives of Ellman's reagent and the dipyridyl disulfides, other suitable indicator dyes useful in the composition of the present invention include the isobenzothiazolone compounds having the structure illustrated as general structural formula (VI):

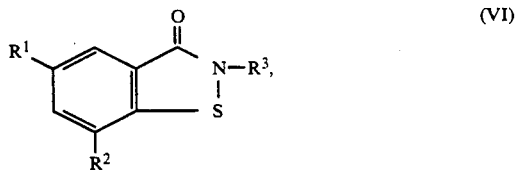

wherein at least one of the $R_1$ and $R_2$ substituents is selected from the group consisting of nitro, arylazo, substituted arylazo, benzylideneamino and substituted benzylideneamino, such that when only one of $R_1$ and $R_2$ is so substituted, one of $R_1$ and $R_2$ can be hydrogen; and the $R_3$ substituent is selected from the group consisting of alkyl, carboxyalkyl, hydroxyalkyl, aminoalkyl, haloalkyl, aryl, carboxyaryl, hydroxyaryl, aminoaryl, heteroaryl, carboxyheteroaryl, hydroxyheteroaryl, aminoheteroaryl, hydroxy, alkoxy, amino and substituted derivatives thereof.

One preferred isobenzothiazolone of structural formulas (VI) includes $R_1$ as nitro and $R_2$ as hydrogen. Other preferred compounds include, but are not limited to, $R_2$ as hydrogen and $R_1$ as phenylazo; 4-hydroxyphenylazo; 4-nitro-2-methylphenylazo; 2-hydroxy-1-naphthylazo; 2-hydroxy-5-methylphenylazo; 2-hydroxy-4-methyl-5-nitrophenylazo; 4-hydroxy-1-naphthylazo; 4-hydroxy-3-methyl-1-naphthylazo; 4-hydroxy-5-aza-1-naphthylazo; 2-amino-1-naphthylazo; 1-hydroxy-2-naphthylazo; 1-hydroxy-2-(N-dimethylaminopropylcarbamoyl)-4-naphthylazo; 3-N,N-dimethylaminopropylcarboxyamido-1-hydroxy-4-naphthylazo; 1-hydroxy-4-methoxy-2-naphthylazo; 2-hydroxy-3-carboxy-1-naphthylazo; 1-hydroxy-3,6-disulfonate-2-naphthylazo; 2,3-dihydroxy-1-naphthylazo, and 2-hydroxy-3,5-dimethyl-1-phenylazo. Another particularly useful compound of general structural formula (VI) includes the substituted benzylideneamino, 2,4-dinitrobenzylideneamino as $R_1$, and $R_2$ as hydrogen. Other useful indicator dyes include, but are not limited to, $R_1$ as hydrogen and $R_2$ as 2-hydroxy-1-naphthylazo or 4-hydroxy-1-phenylazo.

To achieve the full advantage of the present invention, an isobenzothiazolone of general structural formula (VI) includes an $R_3$ substituent selected from the group consisting of alkyl, aryl, heteroaryl, hydroxy, alkoxy, phenyl and amino. These moieties, in turn, can be substituted with functional groups, such as aminoalkyl, aminoaryl, carboxyalkyl, carboxyaryl, hydroxyalkyl, hydroxyaryl, and haloalkyl, selected to provide suitable chemical, i.e. reactivity, or physical, i.e. solubility, properties.

In general, a compound having the structural formula (VI) is capable of detecting and measuring the presence or concentration of thiols, particularly in aqueous media. Thus, the method of the present invention comprises detecting and measuring the presence and concentration of a thiol by the degree and intensity of the color transition of a thiol-responsive dye, then correlating the thiol concentration to the concentration of DHBA in the test sample.

The indicator dyes of general structural formula (VI), upon interaction with a thiol, exhibit a color of longer wavelength and extinction than the color exhibited by Ellman's reagent and derivatives of Ellman's reagent. Accordingly, these more highly-colored reduced dyes exhibit a more easily differentiated and resolved color transition, and the color transition can be detected more easily and accurately in the presence of common interfering substances present in whole blood, plasma, serum, urine and other biological samples.

Therefore, an indicator dye of general structural formula (VI) undergoes a color transition when the indicator dye interacts with the 6,8-dimercaptooctamide generated in Eq. 3 of the scheme to detect DHBA. This interaction is illustrated generally as Eq. 4, and more particularly as Eq. 4b:

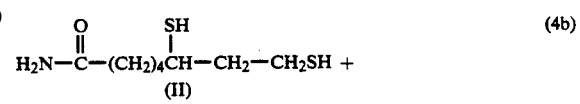

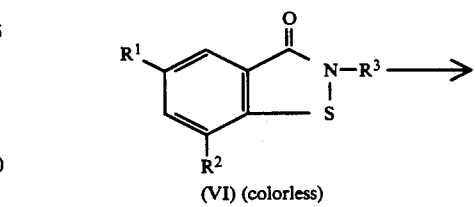

(VI) (colorless)

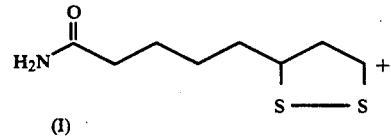

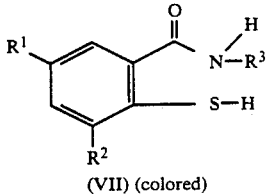

(VII) (colored)

Upon contacting the 6,8-dimercaptooctamide (II), the indicator dye (VI) undergoes a thiol-mediated reduction to form the colored reduction product (VII). The degree and intensity of the color transition are proportional to the amount of 6,8-dimercaptooctamide generated in the test sample, and, in turn, the amount of 6,8-dimercaptooctamide that is generated is proportional to the amount of DHBA in the test sample.

Therefore, in accordance with the method and composition of the present invention, a suitable indicator dye is a compound that is thiol-responsive, undergoes a sufficient color transition upon interaction with a thiol, and exhibits suitable physical properties, such as sufficient solubility in aqueous media. A suitable thiol-responsive indicator dye has a characteristic UV-visible spectrum that changes after interaction with a thiol. Preferably, the change in the UV-visible spectrum is sufficiently large such that the color transition can be detected either visually or instrumentally. Such thiol-responsive indicator dyes are useful for detecting a thiol produced by the reduction of disulfides. Specifically, the thiol-responsive indicator dyes are capable of detecting 6,8-dimercaptooctamide produced by the reaction of LADH and NADH with D,L-lipoamide. Because NADH is generated by the oxidation of a substrate by its particular dehydrogenase, a combination of these compounds is capable of indirectly detecting the amount of such substrates in a test sample. A typical NADH-generating system includes DHBA dehydrogenase and its substrate, DHBA.

Therefore, the indicator reagent composition of the present invention, including a thiol-responsive indicator dye; DHBA dehydrogenase; NAD; D,L-lipoamide; and LADH, is utilized in an improved method to determine the presence or the concentration of DHBA, and therefore ketone bodies, in liquid test samples. It has been demonstrated that the indicator reagent composition interacts with DHBA to produce a differentiable and measurable color transition, either visually or by instrument. Furthermore, in addition to the essential ingredients described above, the indicator reagent composition of the present invention also can include a sufficient amount of various optional ingredients, like a buffer.

For example, test samples often have a pH outside the desired pH range for the assay of interest and therefore a buffer is added to the indicator reagent composition. Accordingly, it has been demonstrated that any of various known types of buffers, if needed, can be included in the indicator reagent composition of the present invention. The buffer is especially important in a commercially-acceptable dry phase test strip to maintain the indicator reagent composition at a sufficient pH to maintain the stability of the indicator reagent composition and to produce the desired color transition in the thiol-responsive indicator dye during the assay.

A buffer is included in the indicator reagent composition of the present invention usually in a concentration of between about 100 mM and about 600 mM, although in particular situations the concentration of the buffer can be above or below this range. It has been found that for optimum assay results, the pH of the indicator reagent composition generally should be maintained at a slightly alkaline to a neutral pH value. Therefore, a pH of from about 7 to about 8.5, and preferably of from about 7 to about 8, provides a more stable indicator reagent composition and a more easily differentiable color transition in the assay for DHBA.

Therefore, an indicator reagent composition of the present invention is buffered to a suitable pH with a buffer such as acetate; BICINE; phthalate; borate; trichloracetate; sulfosalicylate; phosphate; tartarate; citrate; succinate; maleic acid; 2,2-bis(hydroxymethyl)-2,2',2''-nitrilotriethanol; 3,3-dimethylglutaric acid; 3-N-morpholinopropanesulfonic acid (MOPS); malonic acid; 1,3-bis[tris(hydroxymethyl)methylamino]propane (Bis-TRIS); tris(hydroxymethyl)aminomethane (TRIS); tris(hydroxymethyl)aminomethane-maleic acid (TRIS-maleate); tris(hydroxymethyl)aminomethane-malonic acid (TRIS-malonate); 3-N-(trishydroxymethyl)methylamino-2-hydroxypropane sulfonic acid (TAPSO); 2-([tris(hydroxymethyl)methyl]amino)ethanesulfonic acid (TES); 1,4-piperazinebis(ethanesulfonic acid) (PIPES); 4-morpholinoethanesulfonic acid (MES); N-2-hydroxyethylpiperazine-N'-2-ethanesulfonic acid (HEPES); and other suitable buffers as are well known in the art, or combinations thereof.

In addition to the essential ingredients, other optional ingredients, in addition to the buffer, that do not materially alter the nature or the function of the essential ingredients, and that do not interfere with the assay for DHBA, also can be included in the indicator reagent composition. For example, the indicator reagent composition optionally can include a compound to improve the setting of the test pad of the test device by the test sample and to stabilize the reduced indicator dye. This compound usually is an anionic surfactant or a nonionic surfactant. An anionic surfactant, such as a long carbon chain sulfate or sulfonate, like sodium dodecyl sulfate, dioctyl sodium sulfosuccinate and sodium dodecylbenzene sulphonate, is the preferred surfactant. Nonionic surfactants, such as an octoxynol, a nonoxynol or an ethoxylated fatty alcohol, also can be included in the indicator reagent composition of the present invention. The surfactant is included in the indicator reagent composition in a concentration of from 0 mM to about 200 mM, and preferably in a concentration of from about 50 mM to about 200 mM.

The indicator reagent composition also can include a polymeric material that improves the stability and uniformity of the color transition of the test device. Suitable polymeric materials include, but are not limited to, polyvinylpyrrolidone, polyvinyl alcohol, gum arabic, gelatin, algin, carrageenan, casein, albumin, methyl cellulose and similar natural and synthetic polymeric materials. The preferred polymeric material is a polyvinylpyrrolidone of average molecular weight 40,000 and available commercially from GAF Corp., New York, N.Y. The polymeric material generally is included in the indicator reagent composition in an amount ranging from 0% to about 5%, and preferably from about 1% to about 4%, by total weight of the indicator reagent composition.

In addition, to improve the color resolution and differentiation of the color transition in a chromogenic assay for DHBA, inert background dyes can be included in the indicator reagent composition. Suitable background dyes include, but are not limited to, ethyl orange (4-(4-diethylaminophenylazo)benzenesulfonic acid); Orange G (4-(2-hydroxy-(7,9 sodium disulfonate)-1-naphthylazo)benzene); disperse orange 11, 13, or 25; calcomine orange; methyl orange; and orange II (4-(2-hydroxy-1-naphthylazo)benzenesulfonic acid), or combinations thereof. A background dye is included in the indicator reagent composition of the present invention in a concentration ranging from 0 mM to about 2 mM, and preferably ranging from about 0.1 mM to about 1 mM.

The carrier vehicle for the ingredients included in the indicator reagent composition includes water. However, because of the limited water solubility of particular ingredients included in the indicator reagent composition, organic solvents such as methanol, ethanol, isopropyl alcohol, ethylene glycol, propylene glycol, acetone, dimethylformamide, dimethylsulfoxide, acetonitrile, ethyl acetate and similar solvents can be included in the carrier vehicle. The selection of a suitable organic solvent or solvents, in addition to water, to include in the carrier vehicle of the indicator reagent composition is within the capability of those skilled in the art of designing diagnostic assays.

The amount of organic solvent present in the indicator reagent composition generally is in the range of from 0% to about 90%, and preferably from about 10% to about 70%, by weight of the carrier vehicle A carrier solvent comprising water and an organic solvent, like methanol or ethanol, is especially preferred because a carrier matrix impregnated with the indicator reagent composition can be dried within a few to several minutes.

As previously described, the indicator reagent composition undergoes a color transition upon contact with a test sample to demonstrate the presence of DHBA. Furthermore, the intensity and degree of the color transition are used to quantitatively determine the concentration of DHBA. In accordance with an important feature of the present invention, it has been demonstrated that an indicator reagent composition of the present invention provides a sufficiently resolved and differentiated color transition such that the amount of DHBA in a test sample can be measured and accurately determined without the use of color-measuring instruments, such as spectrophotometers or calorimeters. However, if desired, such color-measuring instruments can be used to measure the difference in color degree and intensity between the test sample and a solution having a known concentration of DHBA.

Accordingly, an assay for DHBA that utilizes an indicator reagent composition of the present invention improves the accuracy and reliability of the assay and also increases physician confidence in the assay. Additionally, because of the number of assays for ketone bodies being performed at home by the untrained patient, as opposed to trained physicians or technicians in the laboratory, it is imperative to provide accurate and reliable quantitative assay methods for the ketone body content in a biological fluid.

As discussed above, all previous attempts to develop an accurate, routine test for DHBA have been based on unstable tetrazolium chemistry. In contrast, the present invention utilizes the highly-stable DHBA dehydrogenase and LADH enzymes and a thiol-sensitive indicator dye in a test for DHBA in a dry reagent test strip format. To demonstrate the increased stability of the thiol-responsive indicator dyes used in the indicator reagent composition of the present invention, light was used in a stress study comparing the stability of the tetrazolium dye, iodonitrotetrazolium chloride (INT), to the stability of the isobenzothiazolone compound of general structural formula (VI) wherein $R_1$ is nitro, $R_2$ is hydrogen and $R_3$ is 3-(dimethylamino)propyl, having the nomenclature N-3-(dimethylaminopropyl)-5-nitroisobenzothiazol-3-one and termed IBTZ-I.

FIG. 1 demonstrates the increased stability of the thiol-responsive indicator dyes utilized in the present invention over the tetrazolium dyes used in the prior art. FIG. 1 shows that the percent reflectance for IBTZ-I is essentially unaffected during the course of a 60 minute exposure to combined daylight and ultraviolet radiation. For IBTZ-I the percent reflectance at 460nm decreased only from about 68% to about 62%; whereas for INT, for a 60 minute exposure to light, the percent reflectance measured at 520nm decreased substantially from about 68% to about 20%. In this comparative study, each dye was incorporated in an equimolar amount into individual crosslinked gelatin films. Each film incorporating a dye was exposed to combined daylight and ultraviolet radiation, and the percent reflectance at the appropriate wavelength was measured at the onset of light exposure, then after 5 minutes, 10 minutes, 15 minutes, 30 minutes, 45 minutes and 60 minutes of exposure, respectively. FIG. 1 shows that the gelatin film including INT demonstrates a continuous drop in percent reflectance over time, thereby demonstrating the instability of INT compared to IBTZ-I. It should be noted that in general, the lower the reflectance measurement, or value, the greater the color development, and, therefore, the greater the amount of indicator affected by light. The change in percent reflectance over time upon exposure to light therefore is a measure of the stability of the indicator reagent composition, and consequently, a measure of the stability of the test strip.

In addition to exhibiting increased stability over tetrazolium dyes, the thiol-responsive dyes used in the present invention also are more selective and do not respond to common components found in biological samples, like ascorbic acid or glutathione, to provide false or inaccurate assay results. In contrast, the tetrazolium dyes are significantly affected by these common test sample components. For example, test strips, including either INT or IBTZ-I incorporated into a crosslinked gelatin matrix, were challenged with solutions having a concentration of ascorbic acid in the range of from 0 mg/dL (milligrams per deciliter) to 50 mg/dL. It was found that a test strip including the tetrazolium dye INT demonstrated a positive response, both visually and instrumentally, to increasing concentrations of ascorbic acid. In contrast, test strips incorporating the isobenzothiazolone dye IBTZ-I were not significantly affected. In addition, test strips incorporating either INT or IBTZ-I were challenged with solutions including from 0 mg/dL to 50 mg/dL glutathione. The test strips incorporating INT exhibited a slight sensitivity to glutathione, whereas test strips incorporating IBTZ-I were unaffected by the thiol moiety present in glutathione.

In addition to demonstrating the improved stability of the indicator dye utilized in the present invention, to demonstrate the new and unexpected results achieved by the method of the present invention, an indicator reagent composition including a thiol-responsive indicator dye; DHBA dehydrogenase;.D,L-lipoamide; LADH; and NAD was used in a dry phase test strip assay for DHBA. The dry phase test strip assay utilizing the indicator reagent composition of the present invention is performed in accordance with methods well known in the art. In general, the assay for DHBA is performed by contacting the whole blood, serum, plasma, urine or other test sample with an analyte detection device that includes the indicator reagent composition. The analyte detection device can be dipped into the test sample, or the test sample can be applied to the analyte detection device dropwise. In the case of whole blood, the highly-colored cellular material can be wiped or blotted from the analyte detection device before examining the detection device for a response. The resulting change in color of the analyte detection device demonstrates the presence of DHBA; and, if so designed, the resulting color transition can be compared to a standardized color chart to provide a quantitative measurement of the concentration of DHBA in the blood, urine or other test sample.

Typically, the analyte detection device is a reagent-impregnated test strip, designed either as a single pad test strip (to assay only for a single analyte) or as a multiple pad test strip (to assay for several analytes simultaneously). For either type of reagent impregnated test strip, the test strip includes a support strip, or handle, normally constructed from a hydrophobic plastic, and a reagent test pad, comprising a bibulous or a nonbibulous carrier matrix incorporating the indicator reagent composition. In general, the carrier matrix is an absorbent material that allows the test sample to move, in response to capillary forces, through the carrier matrix to contact the indicator reagent composition and produce a detectable or measurable color transition. In the assay of a whole blood sample, the carrier matrix generally is not permeable to the cellular material. Therefore, the highly-colored cells can be wiped or blotted from the test pad and not interfere with or mask the assay for DHBA. Furthermore, if the carrier matrix is permeable to the cellular material, persons of ordinary skill in the art are aware of techniques and devices to separate the cellular material from the test sample to eliminate the interfering affects of the cellular material.

The carrier matrix can be any substance capable of incorporating the chemical reagents required to perform the assay of interest, as long as the carrier matrix is substantially inert with respect to the chemical reagents, and is porous or absorbent relative to the soluble components of the liquid test sample. The expression "carrier matrix" refers to either bibulous or nonbibulous matrices that are insoluble in water and other physiological fluids and maintain their structural integrity when exposed to water and other physiological fluids. Suitable bibulous matrices include filter paper, sponge materials, cellulose, wood, woven and nonwoven fabrics and the like. Nonbibulous matrices include glass fiber, polymeric films, and preformed or microporous membranes. Other suitable carrier matrices include hydrophilic inorganic powders, such as silica gel, alumina, diatomaceous earth and the like; argillaceous substances; cloth; hydrophilic natural polymeric materials, particularly cellulose material, like cellulosic beads, and especially fiber-containing papers such as filter paper or chromatographic paper; synthetic or modified naturally-occuring polymers, such as crosslinked gelatin, cellulose acetate, polyvinyl chloride, polyacrylamide, cellulose, polyvinyl alcohol, polysulfones, polyesters, polyacrylates, polyurethanes, crosslinked dextran, agarose, and other such crosslinked and noncrosslinked water-insoluble hydrophilic polymers. Hydrophobic and nonabsorptive substances are not suitable for use as the carrier matrix of the present invention. The carrier matrix can be of different chemical compositions or a mixture of chemical compositions. The matrix also can vary in regards to smoothness and roughness combined with hardness and softness. However, in every instance, the carrier matrix comprises a hydrophilic or absorptive material. The carrier matrix is most advantageously constructed from bibulous filter paper or nonbibulous polymeric films. The handle usually is formed from a hydrophobic material such as cellulose acetate, polyethylene terephthalate, polycarbonate or polystyrene.

If the test strip is designed to assay for DHBA in a test sample, the carrier matrix can be any bibulous or nonbibulous material that allows permeation by the soluble components of the test sample to saturate the test pad of the test strip that is impregnated with the indicator reagent composition. A preferred carrier matrix is a hydrophilic, bibulous matrix, including cellulosic materials, such as paper, and preferably filter paper. To achieve the full advantage of the present invention, in the assay for DHBA in a test sample, the carrier matrix is a hydrophilic, nonbibulous matrix, including polymeric films, such as a polyurethane or a crosslinked gelatin. Such polymeric films possesses all of the qualities required of a carrier matrix of the present invention, including suspending and positioning both the essential ingredients and any optional ingredients included in the indicator reagent composition, and permeability of the soluble components of the test sample through the carrier matrix.

To achieve the full advantage of the present invention, the indicator reagent composition is impregnated into a suitable carrier matrix and utilized in a dry phase test strip for the assay of DHBA in a test sample. The method of the present invention affords an economical, accurate and reliable assay, that can be performed at home or in the laboratory, for the presence or concentration of DHBA, and therefore ketone bodies, in a test sample. In addition, the method of the present invention allows detection, differentiation and measurement of a low concentration of DHBA in the test sample therefore making the assay more useful clinically.

In accordance with the method of the present invention, to perform a dry phase test strip assay for DHBA, a methanolic solution, including from about 10 mM to about 200 mM of a thiol-responsive indicator dye, such as Ellman's reagent, a derivative of Ellman's reagent, a suitable 2,2'- or 4,4'-dipyridyl disulfide or an isobenzothiazolone of general structural formula (VI); and from about 10 mM to about 200 mM of D,L-lipoamide and any other desired optional ingredients, or solvents, first is prepared. A nonbibulous matrix, such as a polyurethane film, or a bibulous matrix, such as filter paper, then is saturated or impregnated with the methanolic solution by immersing or by spraying the methanolic solution onto sheets or precut strips or pads of the polyurethane film or filter paper.

Then, after removing the methanol solvent by drying in a forced air oven at a temperature of from about 40° C. to about 100° C. for about 2 minutes to about 5 minutes, the polyurethane film or filter paper is saturated and impregnated with an aqueous solution including from about 50 units to about 5000 units of DHBA dehydrogenase; from about 100 units to about 2000 units of LADH; from 10 mM to about 500 mM of NAD; and any other desired optional ingredients, surfactants or solvents, like background dyes, either by immersion or by spraying. After a second oven drying at about 40° C. to about 100° C. for approximately 2 minutes to 5 minutes, the twice-saturated or twice-impregnated polyurethane film or filter paper, if necessary, is cut to an appropriate size, such as a pad having dimensions from about 0.2 in. (inch) (0.5 cm) by about 0.5 in. (1.3 cm) to about 0.5 in. (1.3 cm) by about 1 in. (2.5 cm).

It should be understood that it is well within the experimental techniques of those skilled in the art of preparing test devices to determine the proper balance between size of reagent pad, the strength of indicator reagent composition solutions, the amount of test sample, and the method of introducing the test sample to the test strip, such as by pipetting rather than dipping, in order to design a quantitative assay for DHBA utilizing the method and composition the present invention.

The dried, twice-impregnated polyurethane film or filter paper then is secured to an opaque or transparent hydrophobic plastic handle with double-sided adhesive tape. The resulting test strip then is contacted with a fresh, uncentrifuged blood or urine sample for a sufficient time to saturate the test pad with the sample. After waiting a predetermined time, such as from about 0.5 minutes to about 10 minutes, the test strip is examined, either visually or by instrument, for a response. If necessary, the cellular material present in the test sample is wiped or blotted from the test strip before examining the test strip for a response. The color transition, if any, of the test pad reveals the presence or concentration of DHBA in the test sample.

In many cases, simple visual observation of the test strip provides the desired information. If more accurate information is required, a color chart bearing color spots corresponding to various known concentrations of DHBA can be prepared for the particular indicator reagent composition used in the test strip. The resulting color of the test strip after contact with the test sample then can be compared with the color spots on the chart to determine the concentration of DHBA in the test sample. If a still more accurate determination is required, a spectrophotometer or colorimeter can be used to more precisely determine the degree of color transition. In addition, the dry phase test strip assay can be made quantitative by employing spectrophotometric or colorimetric techniques, as opposed to visual techniques, in order to more reliably and more accurately measure the degree of color transition, and therefore more accurately measure the concentration of DHBA in the test sample, especially at lower concentrations, such as below 0.5 mmol/L.

In accordance with one embodiment of the present invention, the following dry phase test strips were prepared to perform a dry phase assay for DHBA. A strip, a pad, or a sheet of a carrier matrix, like a microporous polymeric film or membrane, such as polyurethane film including talc as a filler, first was immersed into a methanolic solution including:

| INDICATOR REAGENT COMPOSITION Formulation #1 First Immersion Solution | |
| --- | --- |
| Ingredient | Concentration |
| Ellman's Reagent (indicator dye) | 8.9 mM |
| D,L-Lipoamide (enzyme substrate) | 75.0 mM |

| -continued INDICATOR REAGENT COMPOSITION Formulation #1 First Immersion Solution | |
| --- | --- |
| Ingredient | Concentration |
| Methanol | q.s. |

Excess indicator reagent composition was removed from the surface of the polyurethane film with a scraper bar. A microporous polyurethane film was used in this example because the polyurethane film exhibits a sufficient wetting ability and sufficient adhesion to the hydrophobic plastic support.

The once-saturated or impregnated polyurethane film then was dried in a forced air oven having a temperature ranging from about 45° C. to about 60° C. for about 2 minutes. After drying, the once-saturated or impregnated polyurethane film then was immersed into an aqueous solution including:

| Second Immersion Solution | |
| --- | --- |
| Ingredient | Concentration |
| DHBA Dehydrogenase (enzyme for DHBA) | 100 units |
| LADH (enzyme for D,L-lipoamide) | 500 units |
| NAD | 50 mM |
| BICINE (buffer, pH-8) | 300 mM |
| Water | q.s. |

The twice-saturated or impregnated polyurethane film then was dried in an oven having a temperature ranging from about 40° C. to about 60° C. for about 5 minutes. The dried and twice-saturated or impregnated polyurethane film then was backed with a double-sided adhesive, and slit into 0.4 inch (1 cm) wide ribbon. This ribbon of polyurethane film incorporating an indicator reagent composition of the present invention then is attached to a polystyrene plastic support by means of the double-sided adhesive. The plastic support including the saturated or impregnated polyurethane film then is slit into 0.2 inch (0.5 cm) wide strips. Accordingly, the plastic support includes a pad having dimensions of about 0.2 inch (0.5 cm) by about 0.4 inch (1 cm) of saturated or impregnated polyurethane film to provide a test pad comprising a polyurethane film carrier matrix incorporating an indicator reagent composition of the present invention.

In addition, it should be understood that the indicator reagent composition of the present invention demonstrates sufficient stability such that the carrier matrix can be saturated or impregnated by immersing the carrier matrix into a single aqueous, or aqueous-alcoholic, solution including all of the essential and optional ingredients of the indicator reagent composition. However, the two step method utilizing two immersions is preferred because certain indicator reagent composition ingredients have relatively low water solubilities, and because certain enzyme preparations are occasionally sufficiently impure to preclude solubilizing a sufficient amount of the indicator reagent composition ingredients.

To demonstrate the new and unexpected results achieved by the method of the present invention, dry phase test strips incorporating an indicator reagent composition of the present invention (Formulation #1) were used to assay standardized solutions including DHBA. Individual test strips were dipped into a series of standardized solutions including from 0 mM to 16 mM of DHBA. Approximately 15 minutes after contacting a standardized DHBA solution, the reflectance of the test pad of the test strip was measured at 440nm (nanometers) on a SERALYZER ® Reflectance Photometer, of the Diagnostics Division of Miles, Inc., Elkhart, IN. The reflectance, R, as taken from the reflectance scale of zero to one, was incorporated into the Kubelka-Munk function:

$$K/S = (1-R^2/2R),$$

wherein K is the absorption coefficient, S is the scattering coefficient and R is reflectance. The reflectance values determined at 440 nm were used to calculate the K/S values. The K/S values are proportional to test strip color, therefore the greater the K/S value, the greater the degree and intensity of the color transition of the test strip.

Figure 2:
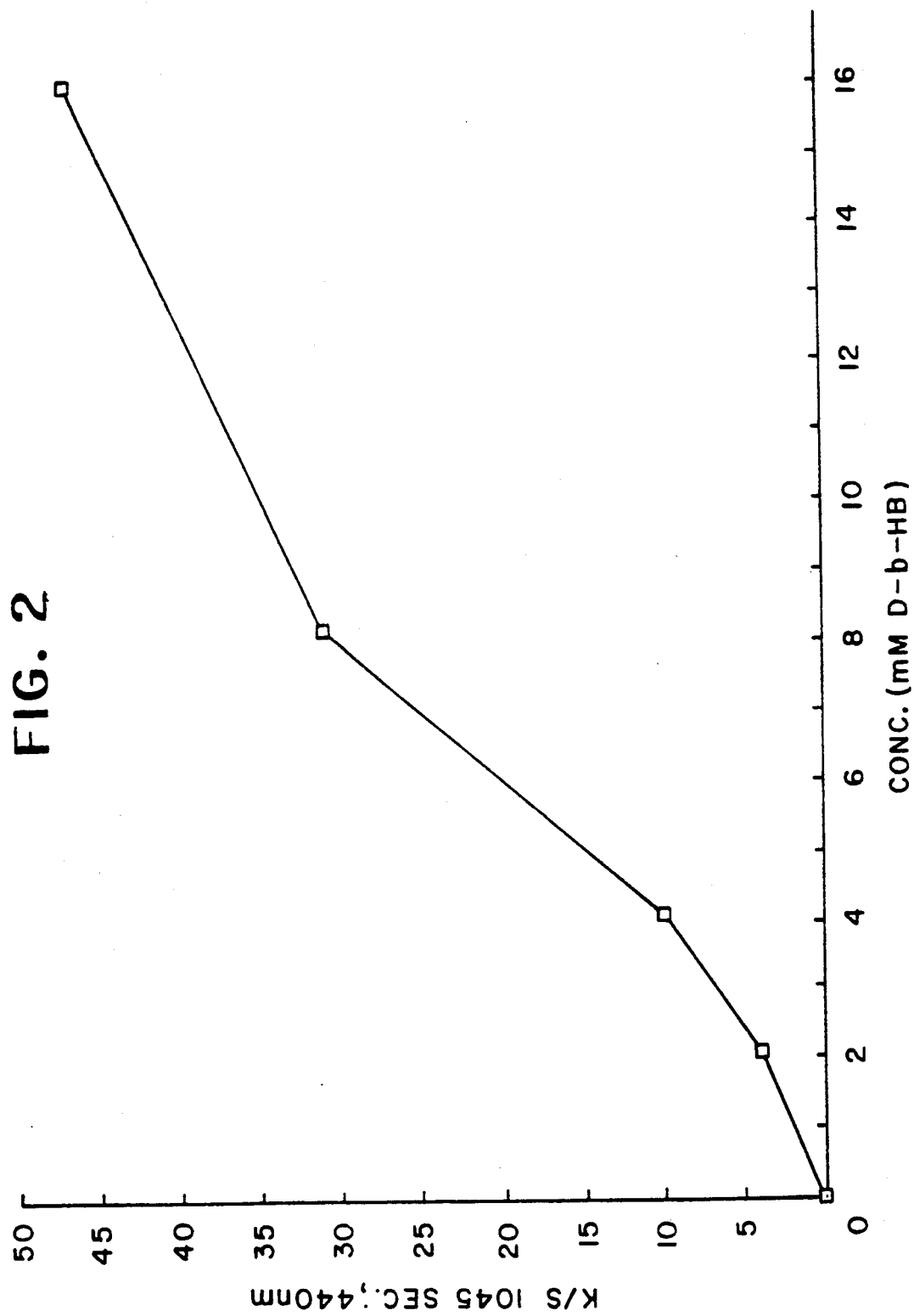
FIG. 2 is a plot of the Kubelka-Munk function (K/S) vs. concentration of DHBA for reflectance values measured at 440nm (nanometers) and 1045 seconds after a dry phase test strip incorporating an indicator reagent composition of the present invention including IBTZ-I contacts a standardized solution of DHBA.

The graph illustrated in FIG. 2 shows the substantially linear response of the color transition of the indicator reagent composition of the present invention with an increasing amount of DHBA in a standardized test sample. In FIG. 2, a K/S value was calculated from reflectance measurements made at 440 nm, 1045 sec. after the test pad contacted the standardized test sample. It was observed that except for the standardized solution including 8 mM DHBA, the K/S value increased linearly with an increasing concentration of DHBA over a range of 0 mM to 16 mM DHBA. The indicator reagent composition utilized in the assays plotted in FIG. 2 was not optimized. Accordingly, after optimization of the indicator reagent composition, the linearity of the response will improve.

To demonstrate that, in addition to Ellman's reagent, other thiol-responsive indicator dyes can be used in the composition of the present invention, a test strip was prepared in the identical manner as described above, except the microporous polyurethane film was saturated or impregnated with the following two solutions, in sequence:

| INDICATOR REAGENT COMPOSITION Formulation #2 | |
|---|---|
| Ingredient | Concentration |
| *First Immersion Solution* | |
| IBTZ-I (indicator dye) | 50 mM |
| D,L-Lipoamide (enzyme substrate) | 200 mM |
| Methanol | q.s. |
| *Second Immersion Solution* | |
| DHBA Dehydrogenase (enzyme for DHBA) | 100 units |
| LADH (enzyme for D,L-lipoamide) | 500 units |

| INDICATOR REAGENT COMPOSITION Formulation #2 | |
|---|---|
| Ingredient | Concentration |
| NAD | 50 mM |
| BICINE (buffer, pH-8) | 300 mM |
| Water | q.s. |

Figure 3:
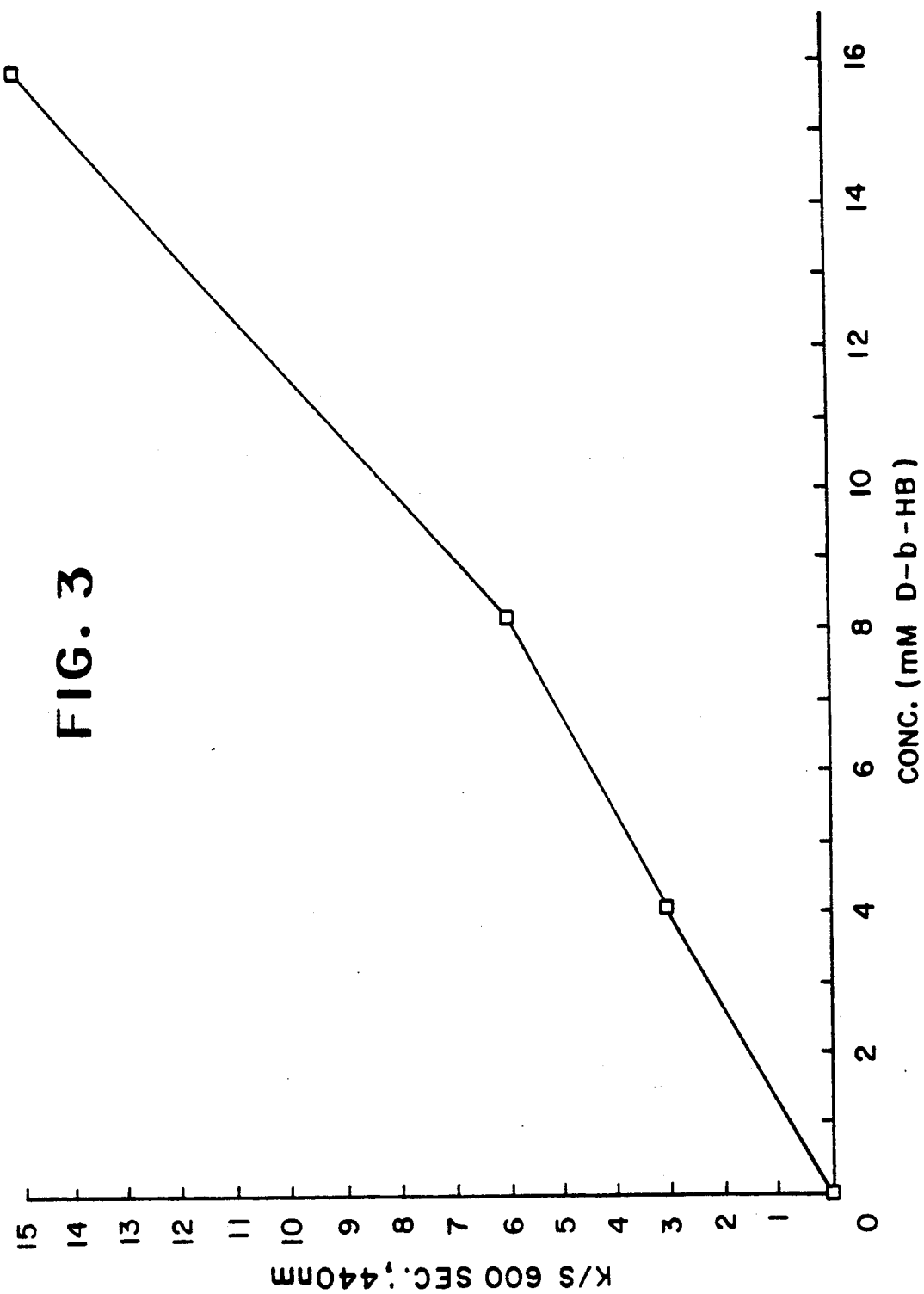
FIG. 3 is a plot of the Kubelka-Munk function (K/S) vs. concentration of DHBA for reflectance values measured at 440nm and 600 sec. after a test strip incorporating an indicator reagent composition of the present invention including IBTZ-I contacts a standardized solution of DHBA.

In Formulation #2, the Ellman's reagent was omitted and replaced by an isobenzothiazolone of general structural formula VI. Test strips incorporating the composition of Formula #2 were used to assay standardized solutions of DHBA over a concentration range of from 0 mM to 16 mM DHBA. The assay procedure was identical to the procedure described above, except the reflectance was measured at 440nm after a 10 minute incubation period. FIG. 3 again shows the substantially linear correlation between K/S values determined at 40 nm and the concentration of DHBA, especially over the concentration range of 0 mM to 8 mM DHBA. This test was repeated with the composition of Formulation #2 saturated or impregnated into a filter paper matrix, and the dose response correlation of the K/S values to DHBA concentrations was essentially identical to those found in test strips using a polyurethane film. Accordingly, it has been demonstrated that a composition of the present invention, including either Ellman's reagent or a substituted isobenzothiazolone of general structural formula (VI), can be corporated into either a bibulous or a nonbibulous carrier matrix to provide a test pad to accurately assay a test sample for DHBA.

In addition to the isobenzothiazolone, IBTZ-I, other isobenzothiazolone compounds having the general structural formula (VI) were included in an indicator reagent composition of the present invention and found to accurately detect the presence or concentration of DHBA in a test sample. In particular, the following TABLE II lists exemplary isobenzothiazolone compounds tested for an ability to detect DHBA in a test sample. It should be noted that other isobenzothiazolone compounds also are useful in the composition and method of the present invention, and that the compounds illustrated in TABLE II are merely nonlimiting examples of suitable isobenzothiazolone indicator dyes. In each of the examples illustrated in TABLE II, the substituent $R_3$ is 3-(dimethylamino)propyl. This particular $R_3$ substituent imparts improved water solubility to the IBTZ compound. The substituents $R_1$ and $R_2$ were varied as indicated in TABLE II. The maximum wavelength ($\gamma_{max}$) for both the oxidized (ox) form and the reduced (red) form of the IBTZ compound also are included in TABLE II.

TABLE II
IBTZ INDICATOR DYES

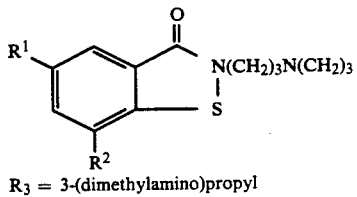

$R_3$ = 3-(dimethylamino)propyl

| | $R^1$ | $R^2$ | $\lambda_{max}$(ox) | $\lambda_{max}$(red) |
|---|---|---|---|---|
| IBTZ I | NO$_2$ 5-nitro | H | 342 | 404 |
| IBTZ II | NO$_2$ 5-nitro | NO$_2$ 7-nitro | 343 | 400 |

TABLE II-continued
IBTZ INDICATOR DYES

Structure: R¹ and R² substituents on a benzene ring fused to a thiazine, with C(=O)N(CH₂)₃N(CH₂)₃ group; $R_3$ = 3-(dimethylamino)propyl

| | R¹ | R² | $\lambda_{max}$(ox) | $\lambda_{max}$(red) |
|---|---|---|---|---|
| IBTZ III | 5-(4-hydroxyphenylazo) [HO—C₆H₄—N=N—] | H | 369 | 408 |
| IBTZ IV | 5-(4-nitro-2-methylphenylazo) [O₂N—C₆H₃(CH₃)—N=N—] | H | 383 | 432 |
| IBTZ V | 5-(2,4-dinitrobenzylideneamine) [O₂N—C₆H₃(NO₂)—C=N—] | H | 381 | 448 |
| IBTZ VI | 5-phenylazo [C₆H₅—N=N—] | H | 355 | 406 |
| IBTZ VII | 5-(2-hydroxy-1-naphthylazo) | H | 490 | 510 |
| IBTZ VIII | 5-(2-hydroxy-5-methylphenylazo) | H | 371 | 456 |
| IBTZ IX | 5-(2-hydroxy-4-methyl-5-nitrophenylazo) | H | 398 | 476 |

TABLE II-continued
IBTZ INDICATOR DYES

R₃ = 3-(dimethylamino)propyl

Structure: benzene ring with R¹ at 5-position, R² at 3-position, C(=O)N(CH₂)₃N(CH₂)₃ and S-R₃ substituents (IBTZ core).

| | R¹ | R² | λ_max(ox) | λ_max(red) |
|---|---|---|---|---|
| IBTZ X | 5-(4-hydroxy-1-naphthylazo) | H | 470 | 484 |
| IBTZ XI | 5-(4-hydroxy-3-methyl-1-naphthylazo) | H | 460 | 512 |
| IBTZ XII | 5-(4-hydroxy-5-aza-1-naphthylazo) | H | 410, 472(sh) | 454 |
| IBTZ XIII | 5-(2-amino-1-naphthylazo) | H | 478 | 490 |
| IBTZ XVI | 5-(1-hydroxy-4-methoxy-2-naphthylazo) | H | 508 | 562 |

Some of the IBTZ compounds illustrated in TABLE II were incorporated into an indicator reagent composition that, in turn, was incorporated into a carrier matrix comprising a crosslinked gelatin film. The indicator reagent composition can be incorporated into the crosslinked gelatin film after the film is formed, or, preferably, the indicator reagent composition is combined with the components comprising the gelatin matrix, including gelatin, polyvinylpyrrolidone, a nonionic surfactant, ethylene glycol and water, to incorporate the indicator reagent composition into the gelatin film as the gelatin film is formed.

To form a gelatin film carrier matrix and simultaneously incorporate the ingredients of the indicator reagent composition into the film, the components of the gelatin film and the ingredients of the indicator reagent composition are admixed and the mixture is cast onto a suitable plastic support with a Mayer rod (#42) to produce an uncrosslinked gelatin film about 100 μ (microns) in thickness. This uncrosslinked gelatin film includes all of the ingredients of the indicator reagent composition. After air drying, an aqueous crosslinking solution, comprising about 1.2% EDAC crosslinking compound, 5% of OLIN 10G nonionic surfactant and 93.8% water, was applied to the uncrosslinked gelatin film to crosslink the film. EDAC is the crosslinking compound 1-ethyl-3-(3-dimethylaminopropyl)carbodiimide, available from Sigma Chemical Co., St. Louis, Mo. Other suitable crosslinking agents include, but are not limited to, glutaraldehyde, disuccinimidyl carbonate, disuccinimidyl oxalate, di-pyridylthionocarbonate and cyclohexyl(morpholinoethyl)carbodiimide metho-p-toluene sulfonate. The crosslinking solution is applied with a Mayer rod (#22) to cast the crosslinking solution at a thickness of about 20 μ. After drying, a test pad of approximately 10 μ in thickness, including an indicator reagent composition of the present invention incorporated into a crosslinked carrier matrix, results.

Figure 4:
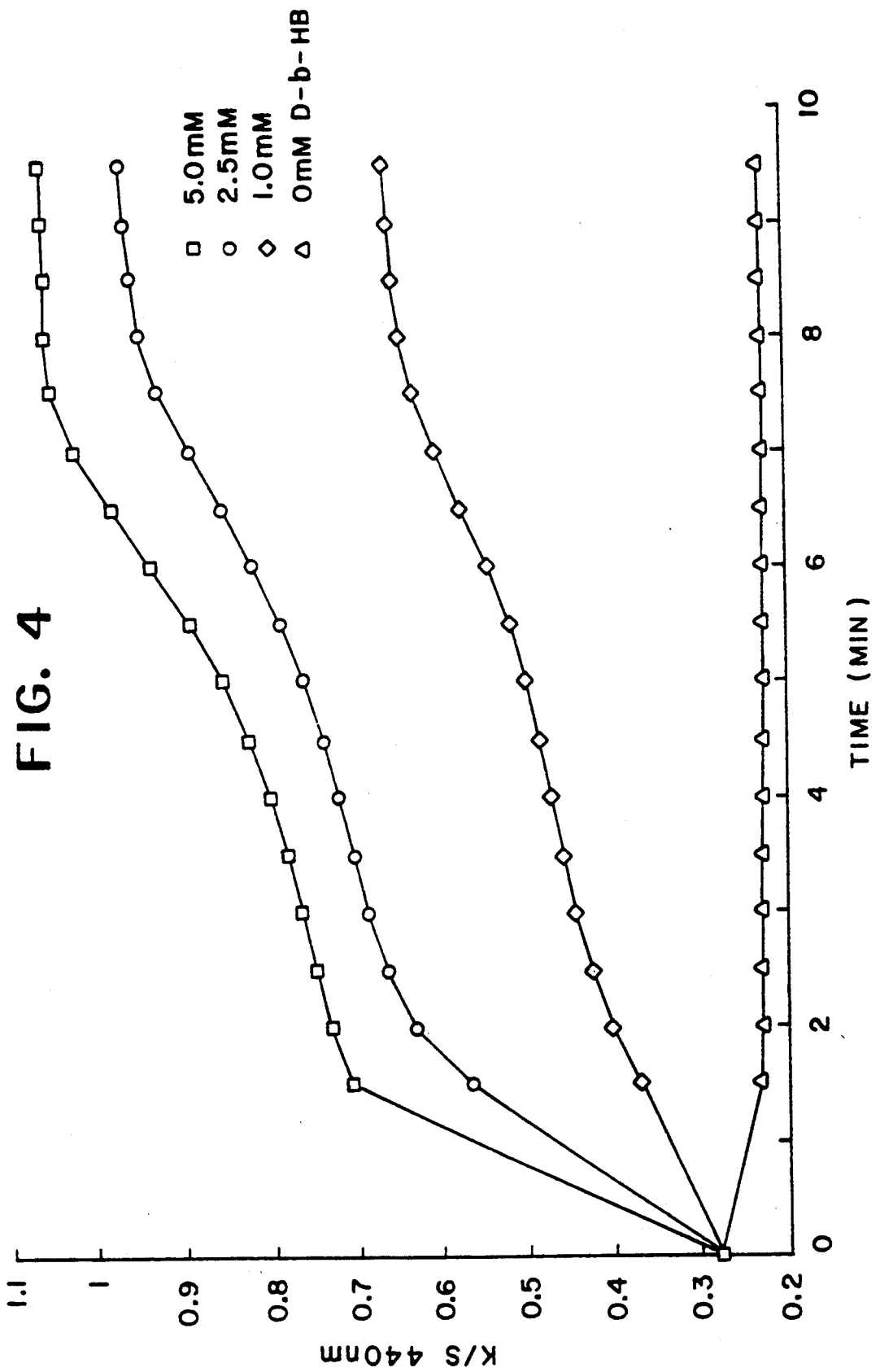
FIG. 4 is a series of plots of the Kubelka-Munk function (K/S) vs. time showing the color transition of a test strip over time for assays of standardized solutions including 0, 1.0, 2.5 and 5.0 mM (millimolar) DHBA, wherein the indicator dye included in the indicator reagent composition was IBTZ-I.

To demonstrate that a variety of isobenzothiazolones of general structural formula VI can be used in the method and composition of the present invention, the indicator reagent compositions of Examples 1 through 8, and illustrated in TABLE III, were prepared and incorporated into a crosslinked gelatin matrix by the above-described method.

including 0, 1.0, 2.5 and 5.0 mM of DHBA. The test strips were assayed by reflectance photometry at 440 nm over a time period of from 0 min. to about 10 minutes after the test strip contacted the test sample. FIG. 4 shows a graph of K/S values at 440 nm vs. time for the assay of the four standardized DHBA solutions. The plots in FIG. 4 demonstrate that a complete color transition, i.e. the endpoint of the assay, occurs at about 8 minutes after the test sample contacts the test pad of the test strip. FIG. 4, and following FIGS. 6, 8, 10, 12 and 13 show that the color transition reaches an endpoint after an incubation period of from about 2 minutes to about 10 minutes, depending upon the particular IBTZ indicator dye used in the indicator reagent composition and upon the concentration of DHBA in the test sample. It also has been found that the color formed in the test pad does not substantially fade due to oxidation of the reduced IBTZ dye for at least about 24 hours, and usually longer Therefore, after determining a sufficient time for a complete color transition, the assayer is free to examine the test pad for a response anytime after the endpoint has been reached, as opposed to examining the test pad at a specific time. Furthermore, the assayer has sufficient time to examine the test pad for a response and obtain an accurate and reliable assay result before the color in the test pad begins to fade.

Figure 5:
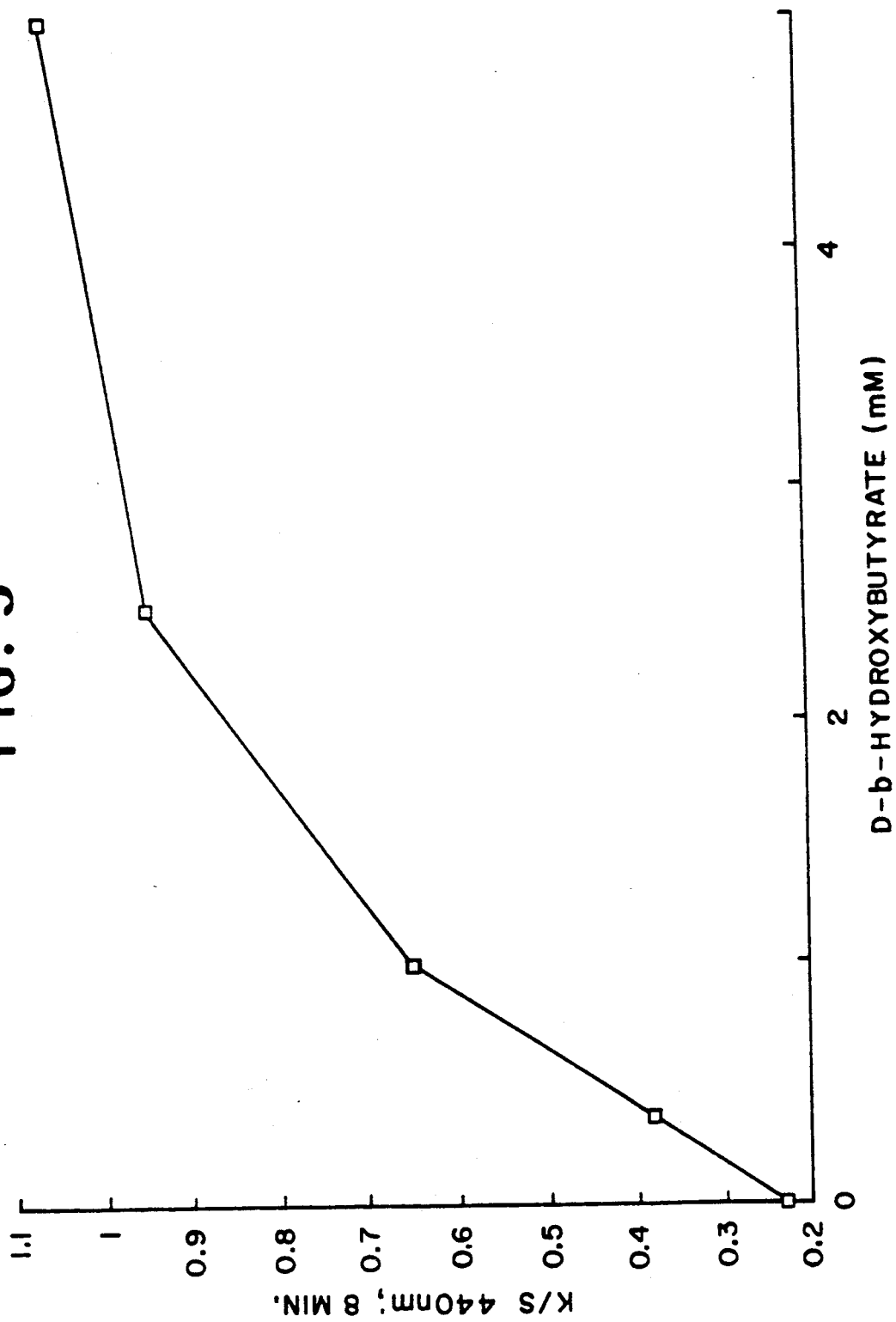
FIG. 5 is a dose response plot of the Kubelka-Munk function (K/S) vs. concentration of DHBA over the range of 0mM to 5mM, wherein the K/S values were determined from the reflectance of the test strip at 440nm after an 8 minute incubation period.

FIG. 5 shows the dose response plot for DHBA concentration vs. K/S at 440 nm after an eight minute incubation. The dose response is substantially linear in the low concentration range of 0 mM to about 2.5 mM DHBA, and linearity at higher concentrations will improve upon optimizing the indicator reagent composition formulation. Accordingly, a test sample, including

TABLE III

| | Indicator Reagent Compositions Including An IBTZ Indicator Dye | | | | | | | |
|---|---|---|---|---|---|---|---|---|
| | Example No. | | | | | | | |
| Ingredients* | #1 | #2 | #3 | #4 | #5 | #6 | #7 | #8 |
| Gelatin (20% w/w)[1] | 5.0 | 5.0 | 5.0 | 5.0 | 5.0 | 5.0 | 5.0 | 5.0 |
| PVP (20% w/w)[2] | 1.0 | 1.0 | 1.0 | 1.0 | 1.0 | 1.0 | 1.0 | 1.0 |
| OLIN 10 G (4% w/w)[3] | 0.5 | — | 0.5 | 0.5 | 0.5 | 0.5 | 0.5 | — |
| TRITON X-100 (4% w/w)[4] | — | 0.5 | — | — | — | — | — | 0.5 |
| Ethylene Glycol | 0.06 | 0.06 | 0.06 | 0.06 | 0.06 | 0.06 | 0.06 | 0.06 |
| IBTZ-I | 0.0125 | 0.0125 | 0.0125 | — | — | — | — | — |
| IBTZ-VII | — | — | 0.0181 | — | — | — | — | — |
| IBTZ-VIII | — | — | — | 0.0165 | — | — | — | — |
| IBTZ-IX | — | — | — | — | 0.0184 | — | — | — |
| IBTZ-X | — | — | — | — | — | 0.0181 | — | — |
| IBTZ-XI | — | — | — | — | — | — | 0.0195 | — |
| IBTZ-XVI | — | — | — | — | — | — | — | 0.0194 |
| NAD | 0.06 | 0.06 | 0.06 | 0.06 | 0.06 | 0.06 | 0.06 | 0.06 |
| D,L-Lipoamide | 0.03 | 0.03 | 0.03 | 0.03 | 0.03 | 0.03 | 0.03 | 0.03 |
| Methanol | 0.8 ml | 0.8 ml | 0.8 ml | 0.8 ml | 0.8 ml | 0.8 ml | 0.8 ml | 0.8 ml |
| LADH | 1.0 ml | 1.0 ml | 1.0 ml | 1.0 ml | 1.0 ml | 1.0 ml | 1.0 ml | 1.0 ml |
| DHBA Dehydrogenase | 1000 units | 1000 units | 1000 units | 1000 units | 1000 units | 1000 units | 1000 units | 1000 units |
| HEPES[5] | 2.3 ml | 2.3 ml | 2.3 ml | 2.3 ml | 2.3 ml | 2.3 ml | 2.3 ml | 2.3 ml |

*Ingredients are present in weight amounts (grams), unless otherwise noted.
[1]Gelatin is 20% by wt. in water; pH 7.5;
[2]PVP is polyvinylpyrrolidone, 20% by weight in water;
[3]OLIN 10 G is a nonylphenol-polyglycidol surfactant, available from Olin Chemical Co., Stamford, Connecticut, 4% by weight in water;
[4]TRITON X-100 is octylphenoxy polyethoxy ethanol including about 9 moles of ethylene oxide, available from Rohm and Haas Co., Philadelphia, PA, 4% by weight in water;
[5]HEPES is the buffer N-2-hydroxyethylpiperazine-N'-2-ethanesulfonic acid; 1M, pH 7.5.

The composition of Example 1, incorporating the ingredients of an indicator reagent composition directly into the components of a gelatin film matrix, was applied to a plastic support and, after crosslinking and drying, the resulting test strip was used to assay for DHBA. Test strips incorporating the composition of Example 1 were used to test standardized solutions an unknown concentration of DHBA can be assayed by determining the K/S value at 440 nm after an eight minute incubation period, and correlating this K/S value to a dose-response plot for standardized DHBA solutions, such as the plot in FIG. 5, to determine the unknown concentration of DHBA in the test sample. It should be noted that the results graphed in FIGS. 4 and 5 are the average results from three replicate assays wherein 30 μL (microliters) of standardized DHBA solution was applied to the test device and excess DHBA solution was blotted from the test device one minute after contact.

Figure 6:
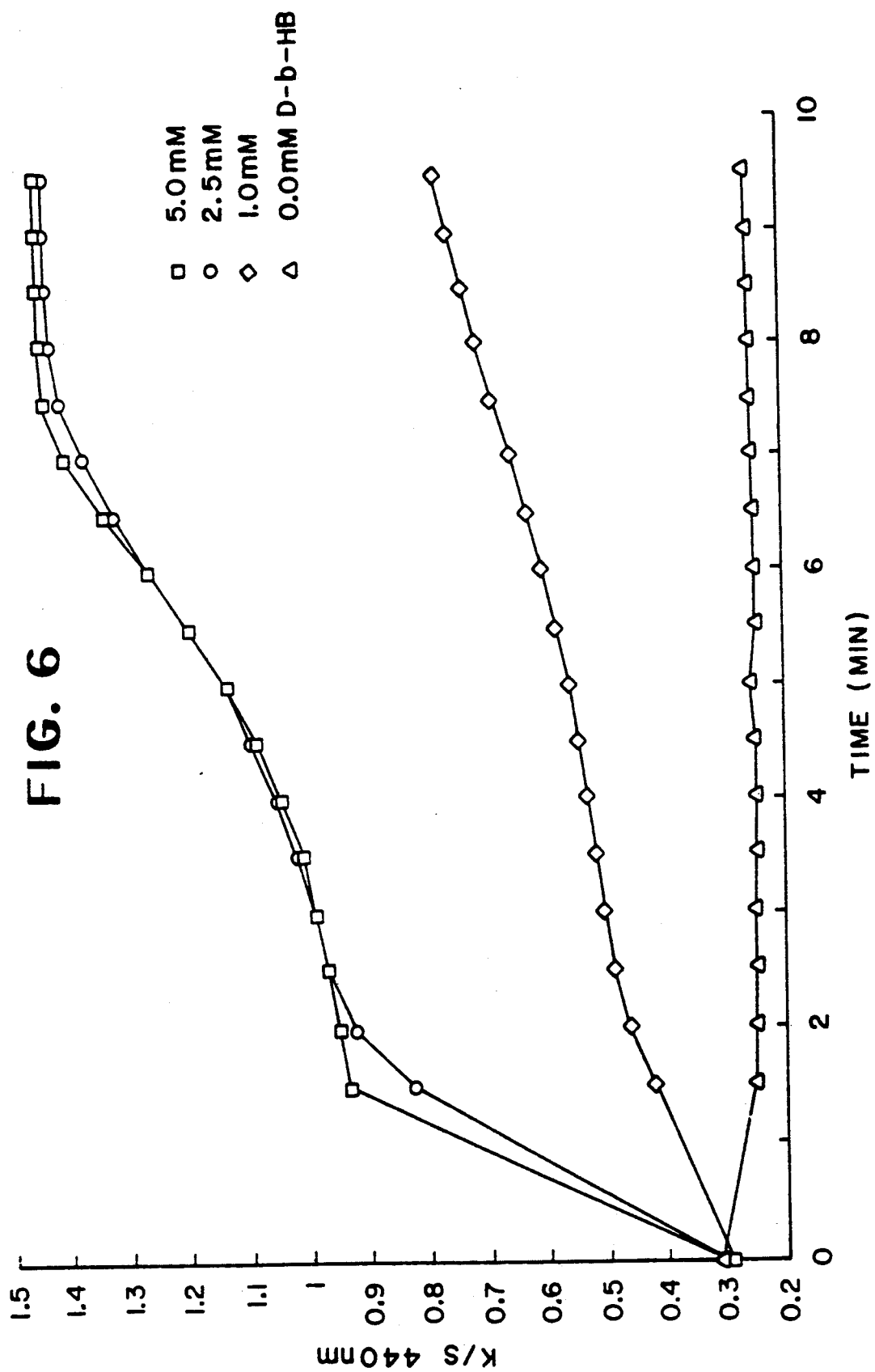
FIG. 6 is a series of plots of the Kubelka-Munk function (K/S) vs. time showing the color transition of a test strip over time for assays of standardized solutions including 0, 0.1, 2.5 and 5.0mM DHBA, wherein the indicator dye including in the indicator reagent composition was IBTZ-I.
Figure 7:
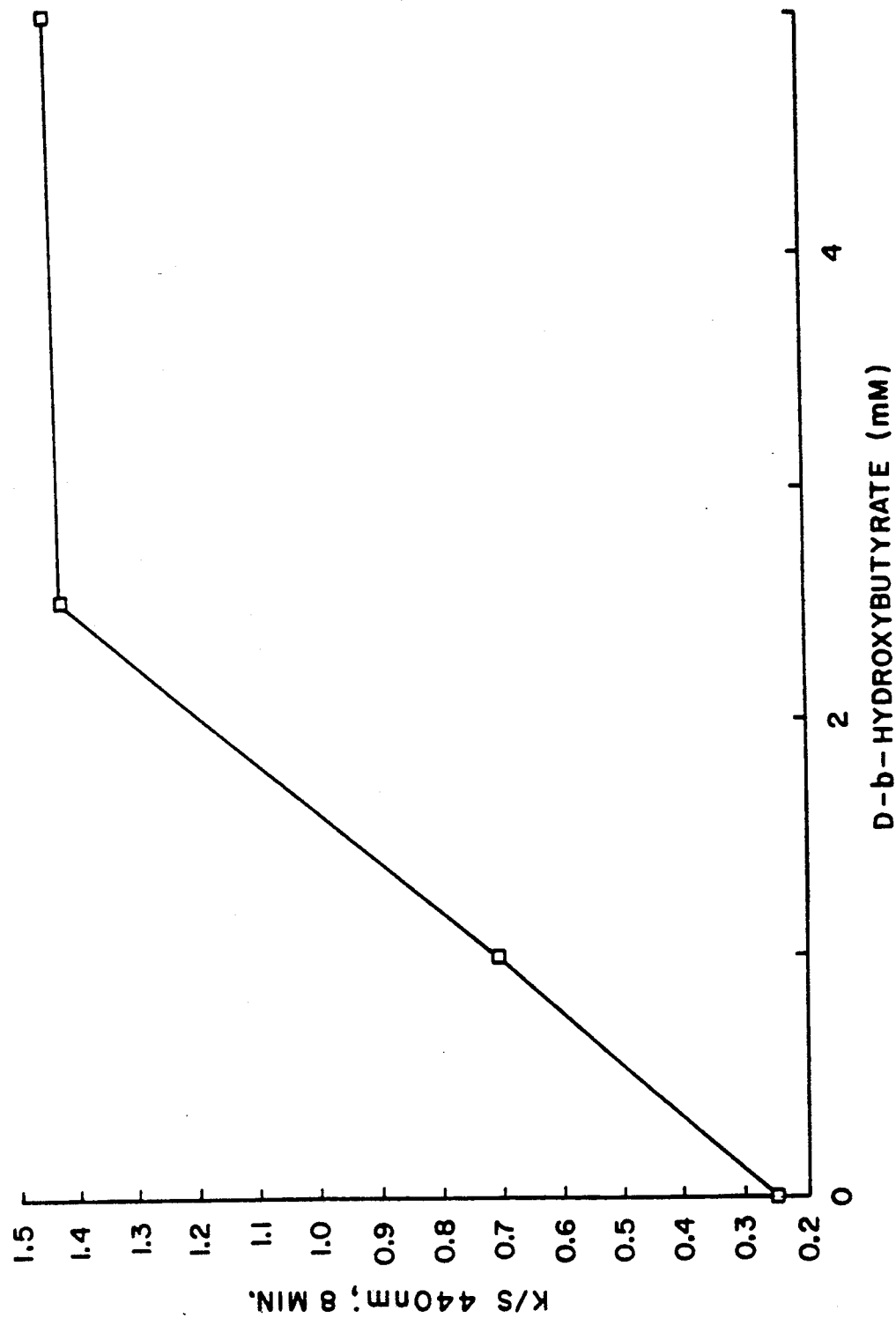
FIG. 7 is a dose response plot of the Kubelka-Munk function (K/S) vs. concentration of DHBA over the range of 0mM to 5mM, wherein the K/S values were determined from the reflectance of the test strip at 440nm after an 8 minute incubation period.

The composition of Example 2 omits the surfactant OLIN 10G, but uses the surfactant TRITON X-100 as a replacement. FIGS. 6 and 7 are similar to FIGS. 4 and 5, and illustrate plots of K/S at 440 nm vs. time and K/S at 440 nm and an 8 minute incubation time vs. concentration of DHBA, respectively. The assay results graphed in FIGS. 6 and 7 are similar to the assay results graphed in FIGS. 4 and 5, however, in FIG. 7, the linearity of the dose response in the range 0 mM to 2 mM DHBA is drastically improved. Accordingly, FIGS. 4 through 7 show that the indicator dye, IBTZ-I, can be included in an indicator reagent composition of the present invention in an assay for low concentrations of DHBA and can provide adequate qualitative assays for high concentrations of DHBA in a test sample.

Figure 8:
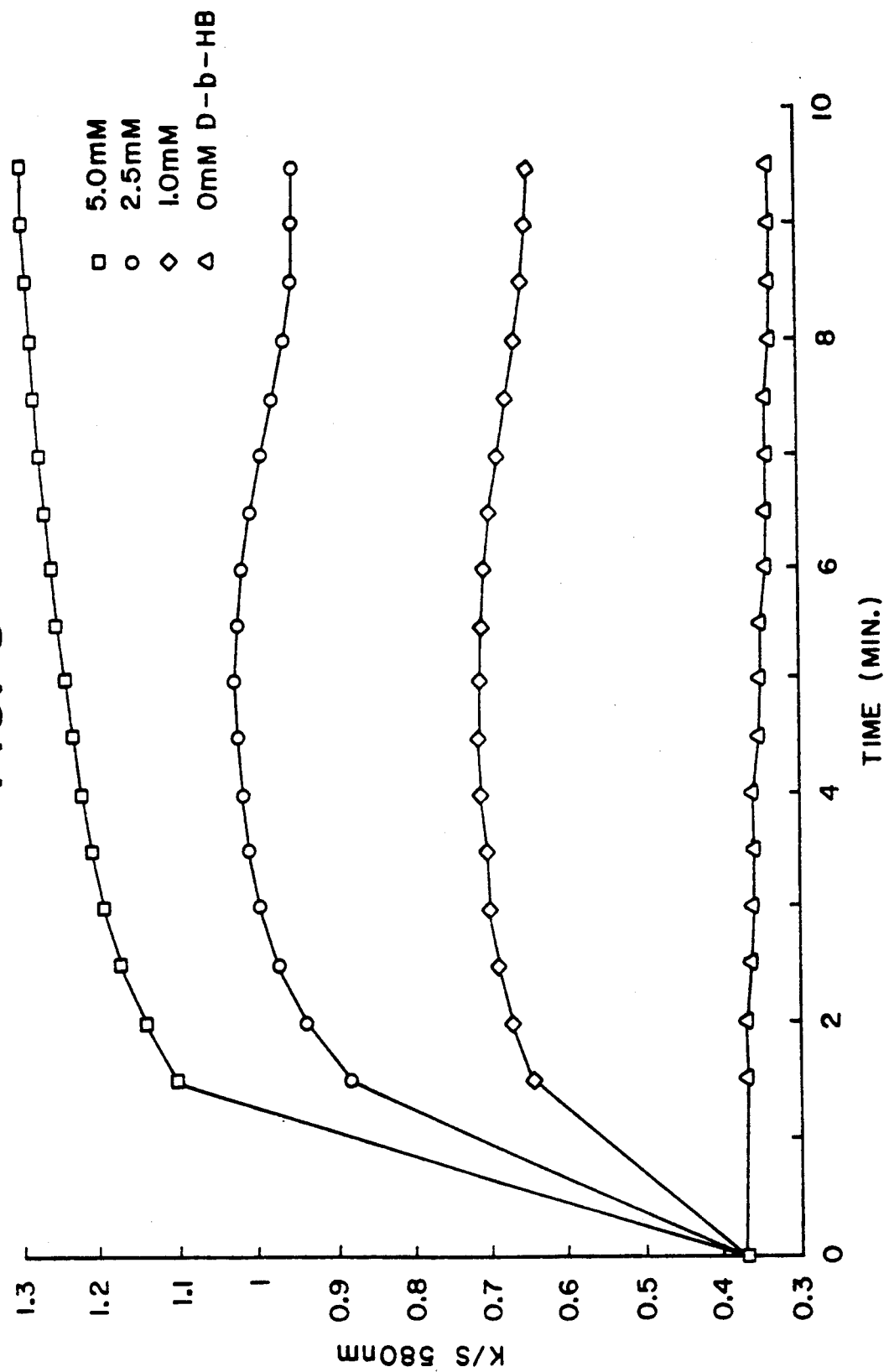
FIGS. 8 and 10 are a series of plots of the Kubelka-Munk function (K/S) vs. time showing the color transition of a test strip over time for assays of standardized solutions including 0, 1.0, 2.5 and 5.0 mM DHBA, wherein the indicator dye included in the indicator reagent composition was IBTZ-VII.
Figure 9:
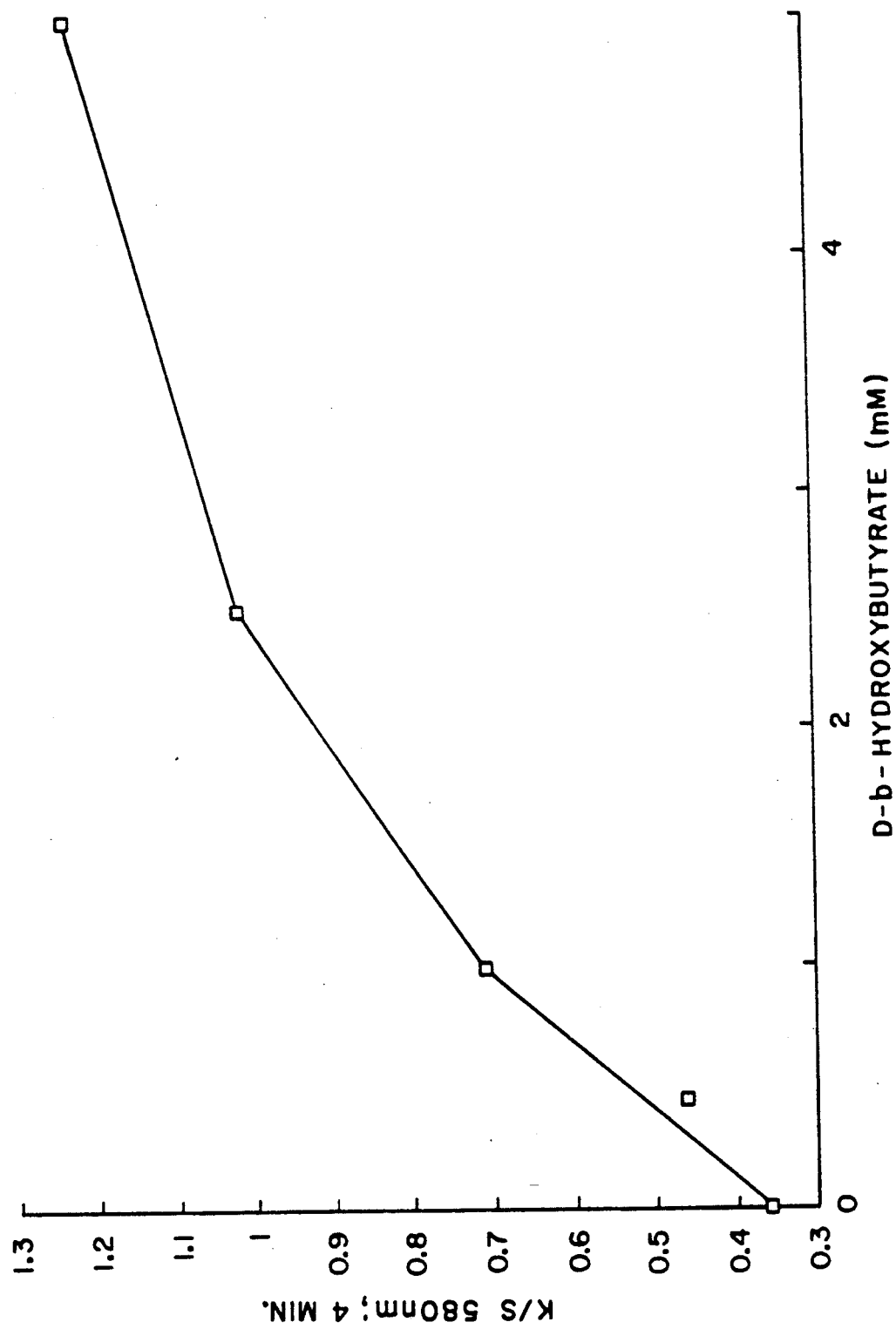
FIGS. 9 and 11 are dose response plots of the Kubelka-Munk function (K/S) vs. concentration of DHBA over the range of 0 mM to 5 mM, wherein the K/S values were determined from reflectance of the test strip at 580nm after a 4 minute incubation period.
Figure 10:
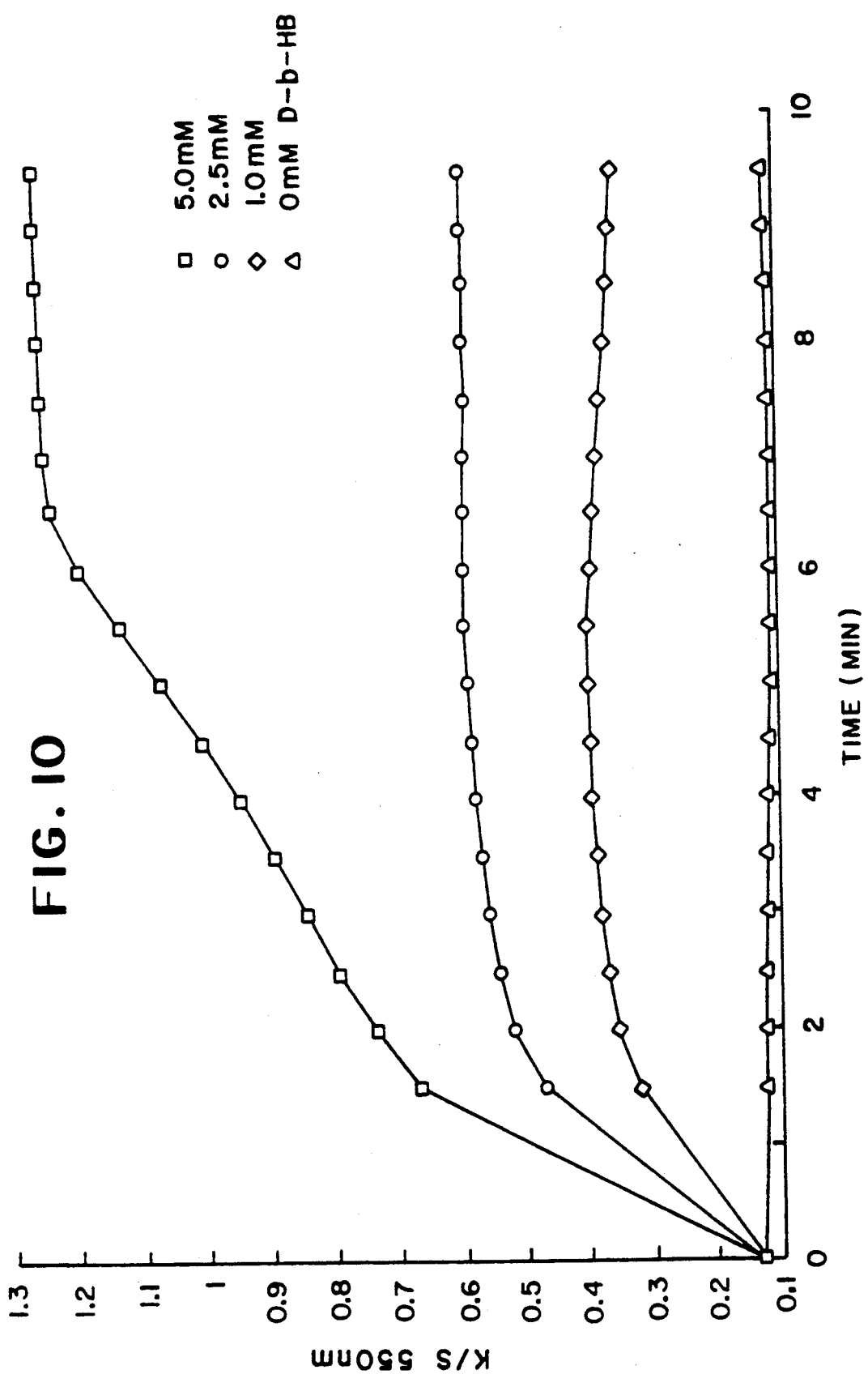
Figure 11:
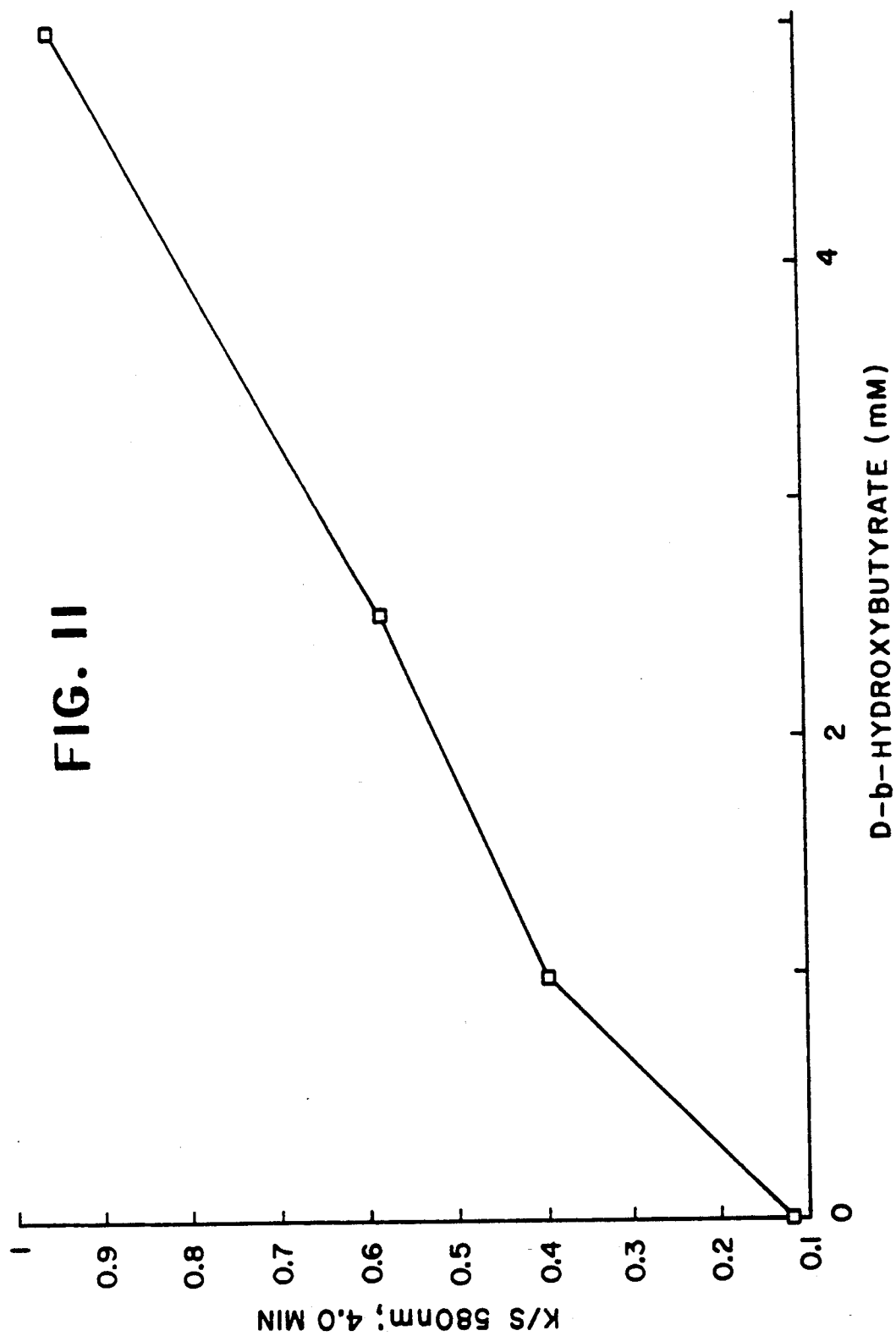
Figure 12:
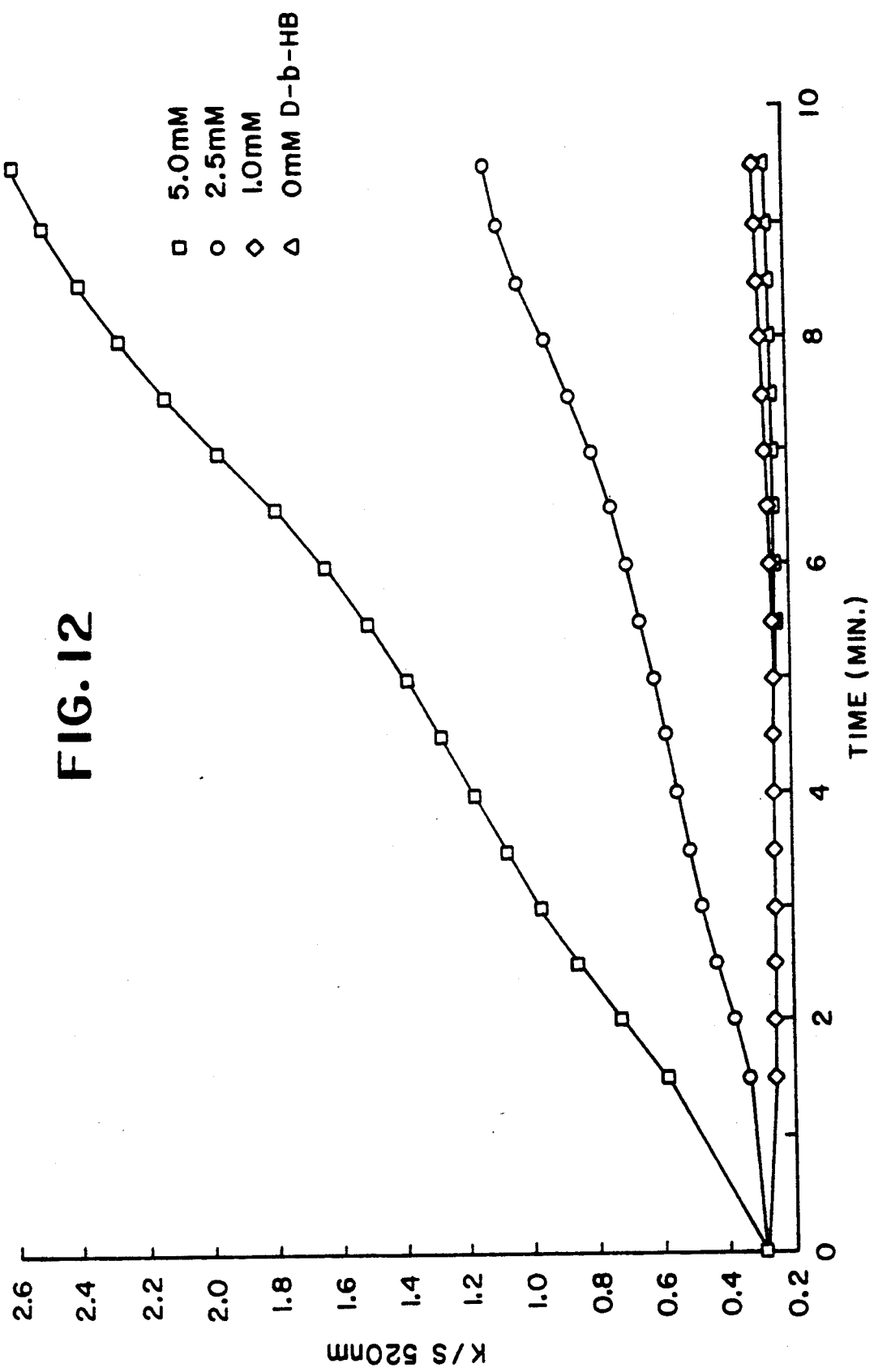
FIG. 12 is a series of plots of the Kubelka-Munk function (K/S) vs. time showing the color transition of a test strip over time for assays of standardized solutions including 0, 1.0, 2.5 and 5.0 mM DHBA, wherein the indicator dye included in the indicator reagent composition was IBTZ-VIII.

The composition of Example 3, including the isobenzothiazolone, N-(3-dimethylaminopropyl)-5-(2-hydroxy-1-naphthylazo)isobenzothiazol-3-one, termed IBTZ-VII, demonstrated an improved ability to detect DHBA in a test sample. FIG. 8 shows that a complete color transition, or the endpoint, for indicator reagent compositions including IBTZ-VII occurs between approximately two and approximately four minutes after the test sample contacts the test pad. Furthermore, the dose response graph presented in FIG. 9 exhibits an excellent dose response of the indicator reagent composition including IBTZ-VII to DHBA over a concentration range of 0 mM to 5 mM, with reflectance measurements made at 580nm and a 4 minute incubation period. The substantially linear character of the graph of FIG. 9 demonstrates that accurate assays for DHBA in a test sample can be achieved Visual assays utilizing the composition of Example 3 also were performed and showed that the color transition of the test pad was from light orange for 0 mM DHBA to dark red orange for 8.0 mM DHBA. FIGS. 10 and 11 illustrate a duplication of the assays illustrated in FIGS. 8 and 9. Therefore, in general, the indicator reagent composition of Example 3 exhibited both a good dose response to DHBA over the range of 0 mM to 5 mM DHBA and a short incubation period of less than five minutes In particular, the short incubation period demonstrated for the composition of Example 3 incorporating IBTZ-VII (FIGS. 8 and 10) can be compared to the longer incubation period required for the composition of Example 4, including IBTZ-VIII, N-3-(dimethylaminopropyl)-5-(2-hydroxy-5-methyphenylazo) isobenzothiazol-3-one (FIG. 12).

The composition of Example 3 again was tested visually for a response to standardized solutions including from 0 mM to 50 mM DHBA. As in the first visual test, it was found that the color of the test strip exposed to a 0 mM DHBA solution (negative) was pale orange. However, a test strip exposed to DHBA solutions including 25 mM to 50 mM DHBA was brilliant purple after from about 3 min. to about 5 min. incubation period. In another example, Example 3A, the composition was identical to the composition of Example 3 except the amount of IBTZ-VII was doubled to 0.0362 g. In visual detection assays for DHBA, test strips incorporating the composition of Example 3A, after a 3 min. incubation period, exhibited a pale orange color for a 0 mM DHBA solution, a red orange color over the range of 2.5 mM to 10 mM DHBA, and a purple color over the range of 25 mM to 50 mM DHBA. The compositions of both Examples 3 and 3A exhibited a color change red to blue in the range of from 10 mM to 25 mM DHBA. More particularly, a test strip incorporating the composition of Example 3 provided the following visual assay results.

TABLE III

Visual Assay Results for DHBA Assays Using Test Strips Incorporating The Composition of Example 3

| Concentration of DHBA (mM) | Observed Color |
|---|---|
| 0 | light pumpkin |
| 0.5–1.0 | deep orange |
| 2.5–5.0 | red orange |
| 10.0–25.0 | brown |
| 50.0 | maroon |

Accordingly, the composition and method of the present invention can be used in a visual assay to determine the presence and semiquantitative concentration of DHBA in a test sample.

Figure 13:
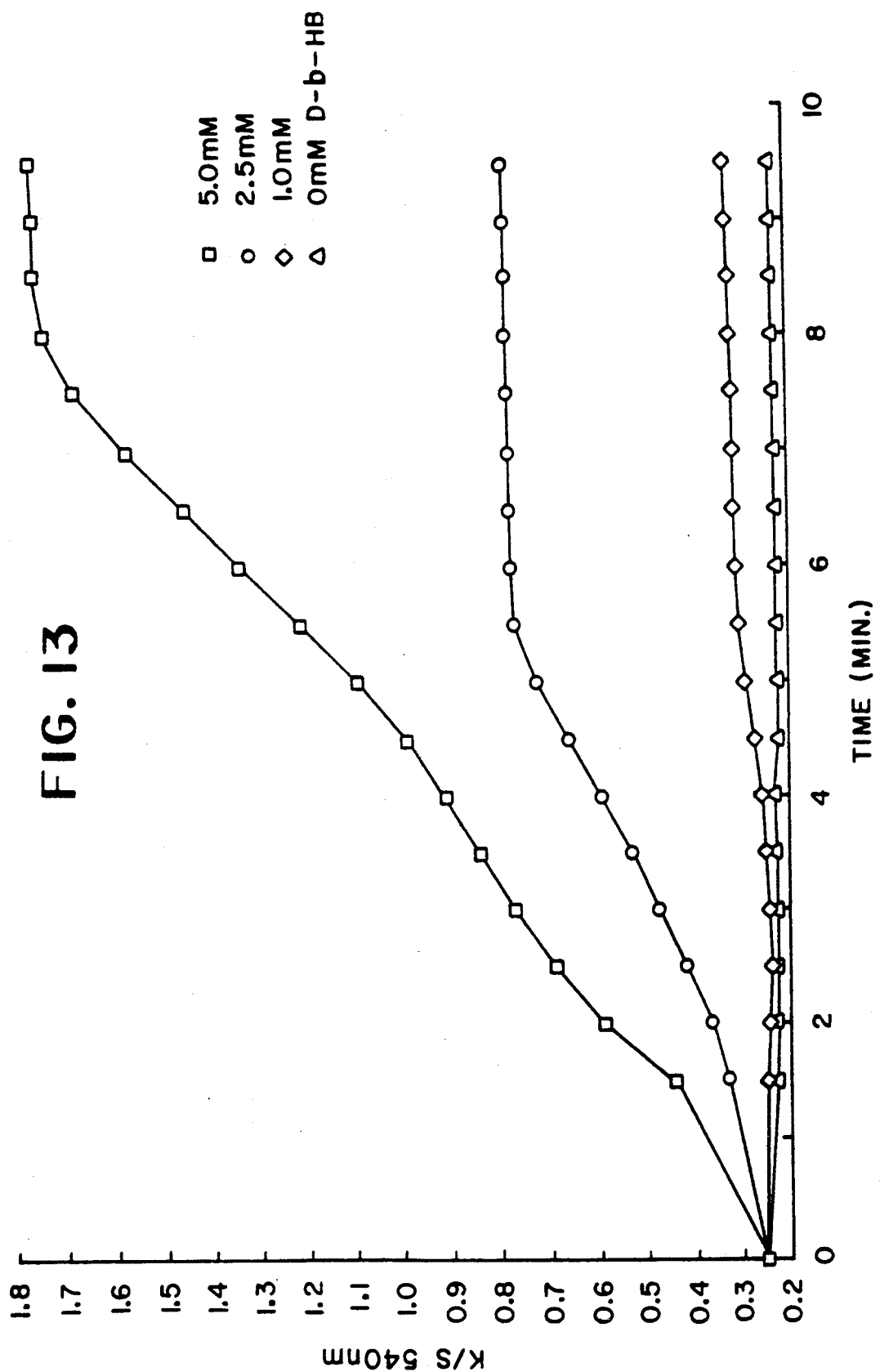
FIG. 13 is a series of plots of the Kubelka-Munk function (K/S) vs. time showing the color transition of a test strip over time for assays of standardized solutions including 0, 1.0, 2.5 and 5.0 mM DHBA, wherein the indicator dye included in the indicator reagent composition was IBTZ-IX.
Figure 14:
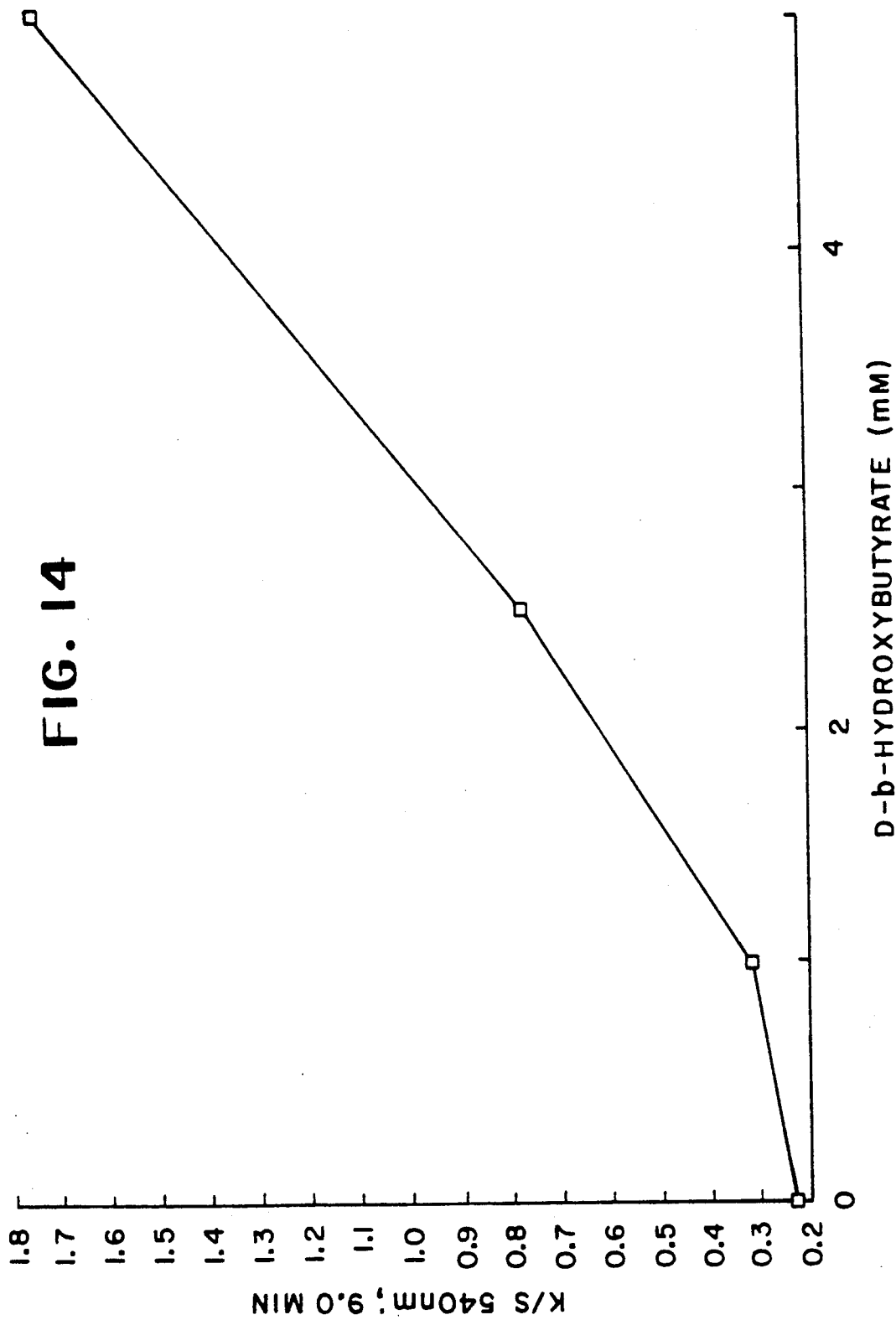
FIG. 14 is a dose response plot of the Kubelka-Munk function (K/S) vs. concentration of DHBA over the range of 0 mM to 5 mM, wherein the K/S values were determined from reflectance of the test strip at 540 nm after a 9 minute incubation period.

Assays results of DHBA utilizing the composition of Example 5, and including the indicator dye IBTZ-IX, or N-3-(dimethylaminopropyl)-5-(2-hydroxy-4-nitro-5-methylphenylazo)isobenzothiazol-3-one, are illustrated on FIGS. 13 and 14. In particular, an indicator reagent composition including the indicator dye IBTZ-IX exhibited a color transition endpoint within about 8 mins. (FIG. 13) and an excellent does response to DHBA concentration, especially at concentrations ranging from about 1 mM DHBA and greater (FIG. 14).

The composition of Example 8, including the thiol-responsive dye, IBTZ-XVI, N-(3-dimethylaminopropyl)-5-(4-methoxy-1-hydroxy-2-naphthylazo)isobenzothiazol-3-one, was used in a test strip to assay standardized solutions including from 0 mM to 50 mM DHBA. The standardized DHBA solution was applied to the test pad of the test strip, then, one minute after contact, the excess standardized solution was blotted from the test pad. After a three minute incubation period, the test pad was examined, visually, for a response. The test pads underwent a color transition and the following colors were observed: 0 mM DHBA—dark pink; 0 5 mM-1.0 mM DHBA—lavender; 2.5 mM -25 mM DHBA—dark royal blue; and 50 mM DHBA—deep blue. Therefore, different IBTZ indicator dyes, and different derivatives of Ellman's reagent, can provide different color transitions over different concentration ranges such that a combination of IBTZ thiol-responsive dyes, or a combination of an IBTZ thiol-responsive dye with Ellman's reagent, a derivative of Ellman's reagent or other thiol-responsive dyes, can be incorporated into an indicator reagent composition of the present invention to achieve a more dramatic and more easily resolvable and differentiated color transition. Such an improved color transition provides a more sensitive and more accurate dry phase test strip assay for DHBA, in particular, and ketone bodies in particular.

From the visual assays and the data presented in FIGS. 1–14, it has been found that a particularly useful IBTZ indicator dye is IBTZ-VII. An indicator reagent composition of the present invention that includes IBTZ-VII exhibits a sufficiently dramatic color transition, from light yellow to purple, to provide a sensitive and accurate assay for DHBA in a test sample. The color transition also is sufficiently resolvable and differentiable, either visually or by instrument, such that an unknown concentration of DHBA in a test sample can be determined. Furthermore, it has been found that the indicator dye IBTZ-VII accelerates the interaction between the indicator dye and 6,8-dimercaptooctamide such that the color transition endpoint is reached within about 1 to 2 minutes, rather than the 5 minutes to 10 minutes required for the other IBTZ indicator dyes, Ellman's reagent and the derivatives of Ellman's reagent. It has been theorized that the structure of IBTZ-VII, illustrated as structural formula (VIII), allows the ortho-hydroxy moiety to stabilize the nitrogen-sulfur ring opening by complexing with an azo-nitrogen atom.

(VIII)

Accordingly, the ability of LADH to react sequentially with DHBA dehydrogenase to generate 6,8-dimercaptooctamide, and thereby cause a color transition in a thiol-responsive indicator dye has provided a sensitive method to accurately assay for DHBA, and therefore ketone bodies, in a test sample, like a biological fluid. The method includes incorporating an indicator reagent composition of the present invention into a dry phase test strip, and using the dry phase test strip to assay whole blood, blood serum, blood plasma, urine or other test samples in either a blot-off, wipe-off or dip-and-read format. The sensitivity of the method of the present invention allows the presence or concentration of DHBA in the test sample to be determined either visually or by instrument.

Furthermore, and in accordance with an important feature of the present invention, the continuing and substantial problems in dry phase test strips for DHBA, including the instability of the tetrazolium indicator dye used in the prior art and the interfering interaction of the indicator reagent composition with common components in the test sample, are essentially eliminated. An indicator reagent composition of the present invention, including a stable, thiol-responsive dye, like Ellman's reagent, a derivative of Ellman's reagent or an isobenzothiazolone dye of general structural formula (VI), essentially eliminates the problem of a false positive assay due to an interaction of the indicator dye with an interferent in the test sample. Such a discovery is an unexpected and surprising improvement in the art of dry phase test strip assays for DHBA in a biological test sample. In addition, the indicator reagent composition has demonstrated the capability of assaying for DHBA in a test sample by utilizing an enzyme-based chemistry that is specific to DHBA, and then couples this enzyme-based chemistry to lipoamide detection chemistry to provide a sensitive and accurate assay for DHBA. Therefore, in accordance with an important feature of the present invention, more accurate and reliable assays for DHBA in whole blood, blood serum, blood plasma, urine and other test samples can be performed by utilizing the indicator reagent composition of the present invention.

In particular, a test pad incorporating a composition of the present invention can be included in a multideterminant test strip to assay for DHBA. If an individual is testing whole blood for glucose to monitor the course of diabetes, the individual also could test for DHBA, simultaneously with the assay for glucose, to monitor the onset of ketosis. Accordingly, the individual does not require two separate test kits to perform two separate assays, and a single, small blood sample can be used for both assays. Furthermore, if an individual is assaying urine, a test pad incorporating a composition of the present invention can be included on a multideterminant test strip to simultaneously assay for glucose and for DHBA to detect ketonuria. In particular, such assays should be able to accurately detect a clinically significant amount of DHBA from 0 mmol/L to about 10 mmol/L DHBA in a whole blood assay, and from 0 mmol/L to about 60 mmol/L DHBA in a urine assay.

The dry phase test strip assays of the present invention for DHBA are most useful for assays performed at home, in private physician laboratories and in emergency rooms. For example, the dry phase test strip assay for DHBA in whole blood could replace urinary ketone test strip assays or tablet assays in the emergency room diagnosis of ketoacidosis. In addition, besides the greater convenience in using blood rather than urine in the emergency room, the whole blood test for DHBA also would diagnose alcoholic ketoacidosis. Such a result is extremely important because in cases of alcoholic ketoacidosis, the conversion of acetoacetate to $\beta$-hydroxybutyrate is essentially complete. Therefore, urinary tests for acetoacetate usually are negative. As a result, the diagnosis of alcoholic ketoacidosis often is missed.

Therefore, the indicator reagent composition of the present invention, comprising a thiol-responsive indicator dye; LADH; DHBA dehydrogenase; D,L-lipoamide; and NAD is sufficiently stable and selective in reactivity to provide an accurate and sensitive DHBA assay. The indicator reagent composition of the present invention also undergoes a more spectacular color transition in response to the concentration of DHBA in a test sample. In general, therefore, an indicator reagent composition of the present invention demonstrates an ability for DHBA dehydrogenase and LADH to interact with their respective substrates sequentially; demonstrates improved stability and selectivity and therefore eliminates the development of an interfering background color in the test pad due to an interaction between the indicator dye and an interferent in the test sample; and increases the useful life of the test strips because of the stability of the indicator dye.

Obviously, many modifications and variation of the invention as hereinbefore set forth can be made without departing from the spirit and scope thereof and therefore only such limitations should be imposed as are indicated by the appended claims.

I claim:

1. A composition capable of exhibiting a sufficient color transition upon contacting a test sample to demonstrate the presence or concentration of D-$\beta$-hydroxybutyrate in the test sample said composition comprising:
   a) D$\beta$-hydroxybutyrate dehydrogenase;
   b) nicotinamide adenine dinucleotide;

c) a disulfide reductase system comprising a disulfide substrate and a disulfide reductase; and d) a thiol-responsive indicator dye.

2. The composition of claim 1 wherein the D$\beta$-hydroxybutyrate dehydrogenase is present in an amount ranging from about 50 units to about 5000 units.

3. The composition of claim 1 wherein the D$\beta$-hydroxybutyrate dehydrogenase is present in an amount ranging from about 90 units to about 500 units.

4. The composition of claim 1 wherein the nicotinamide adenine dinucleotide is present in a concentration ranging from about 10 mM to about 500 mM.

5. The composition of claim 1 wherein the nicotinamide adenine dinucleotide is present in a concentration ranging from about 40 mM to about 100 mM.

6. The composition of claim 1 wherein the disulfide reductase system includes D,L-lipoamide as the disulfide substrate and lipoamide dehydrogenase as the disulfide reductase.

7. The composition of claim 1 wherein the disulfide substrate is present in a concentration ranging from about 10 mM to about 200 mM, and the disulfide reductase is present in an amount ranging from about 100 units to about 2000 units.

8. The composition of claim 1 wherein the disulfide substrate is present in a concentration ranging from about 50 mM to about 150 mM, and the disulfide reductase is present in an amount ranging from about 250 units to about 1000 units.

9. The composition of claim 1 wherein the thiol-responsive dye is present in a concentration ranging from about 10 mM to about 200 mM.

10. The composition of claim 1 wherein the thiol-responsive dye is present in a concentration ranging from about 25 mM to about 150 mM.

11. The composition of claim 1 wherein the thiol-responsive dye is Ellman's reagent.

12. The composition of claim 1 wherein the thiol-responsive dye is an amide derivative of Ellman's reagent or an ester derivative of Ellman's reagent represented by the structural formula $$\underset{O_2N}{\phantom{X}} \overset{O}{\underset{\parallel}{R-C}} - \underset{}{\text{Ar}} - S - S - \underset{}{\text{Ar}} - \overset{O}{\underset{\parallel}{C-R}} \underset{NO_2}{\phantom{X}}$$

wherein the R moiety is the residue of an alcohol or an amine.

13. The composition of claim 12 wherein the R moiety is selected from the group consisting of

—O(CH$_2$CH$_2$O)$_4$H; —N\_/N—CH$_3$;

—NH—N(CH$_3$)$_2$; —N\_/O;

—NH(CH$_2$)$_3$N(CH$_3$)$_2$; and a combination thereof.

14. The composition of claim 1 further comprising a carrier vehicle including water.

15. The composition of claim 14 wherein the carrier vehicle further comprises an organic solvent in an amount ranging from 0% to about 90% by weight of the carrier vehicle.

16. The composition of claim 15 wherein the organic solvent is selected from the group consisting of methanol, ethanol, isopropyl alcohol, ethylene glycol, propylene glycol, acetone, dimethylformamide, dimethylsulfoxide, acetonitrile, ethyl acetate and combinations thereof.

17. The composition of claim 1 having a pH in the range of from about 7 to about 8.5.

18. The composition of claim 1 further comprising from 0 mM to about 600 mM of a buffer; from 0% to about 5% by weight of a polymeric material; from 0 mM to about 200 mM of a surfactant; from 0 mM to about 2 mM of an inert background dye; or combinations thereof.

19. The composition of claim 1 wherein the test sample is a biological fluid.

20. The composition of claim 19 wherein the biological fluid is whole blood, blood serum, blood plasma or urine.

21. The composition of claim 20 capable of determining the concentration of D-$\beta$-hydroxybutyrate in urine in the range of from 0 mmol/L to about 60 mmol/L.

22. The composition of claim 20 capable of determining the concentration of D$\beta$-hydroxybutyrate in whole blood, blood plasma or blood serum in the range of from 0 mmol/L to about 10 mmol/L.

23. A composition capable of exhibiting a sufficient color transition upon contacting a test sample to demonstrate the presence or concentration of D-$\beta$-hydroxybutyrate in the test sample, said composition comprising:

a) from about 50 units to about 5000 units per liter of the composition of D-$\beta$-hydroxybutyrate dehydrogenase;

b) from about 10 mM to about 500 mM of nicotinamide adenine dinucleotide;

c) a disulfide reductase system comprising from about 10 mM to about 200 mM D,L-lipoamide and from about 100 units to about 2000 units per liter of the composition of lipoamide dehydrogenase; and d) from about 10 mM to about 200 mM of a thiol-responsive dye.

* * * * *